US005880334A

United States Patent [19]

Suzuki et al.

[11] Patent Number: 5,880,334

[45] Date of Patent: Mar. 9, 1999

[54] DNA ENCODING PHOSPHOENOLPYRUVATE CARBOXYKINASE, RECOMBINANT VECTOR AND TRANSFORMED PLANT CONTAINING THE SAME

[75] Inventors: Shoichi Suzuki; Masao Arai; Nobuhiko Murai, all of Shizuoka, Japan; Patrick M. Finnegan, Canberra; James Nigel Burnell, Queensland, both of Australia

[73] Assignee: Japan Tobacco Inc., Tokyo, Japan

[21] Appl. No.: 617,801

[22] PCT Filed: Jul. 6, 1995

[86] PCT No.: PCT/JP95/01356

§ 371 Date: May 8, 1996

§ 102(e) Date: May 8, 1996

[87] PCT Pub. No.: WO96/01895

PCT Pub. Date: Jan. 25, 1996

[30] Foreign Application Priority Data

| | | | |
|---|---|---|---|
| Jul. 9, 1994 | [JP] | Japan | 180756 |
| May 10, 1995 | [JP] | Japan | 136000 |

[51] Int. Cl.[6] .......... A01H 5/00; C12N 15/82; C12N 15/63; C07H 21/04

[52] U.S. Cl. .......... 800/298; 435/320.1; 536/23.6; 800/320.2

[58] Field of Search .......... 435/320.1; 536/23.6; 800/205, DIG. 57

[56] References Cited

FOREIGN PATENT DOCUMENTS 0507698 10/1992 European Pat. Off. .
WO94-00977 1/1994 WIPO .

OTHER PUBLICATIONS

Kim et al. Molecular cloning of cucumber phosphoenolpyruvate carboxykinase and developmental regulation of gene expression. Plant Molecular Biology. 26:423–434, Oct. 1994.

Osteras et al. Molecular and expression analysis of the *Rhizobium meliloti* phosphoenolpyruvate carboxykinase (pckA) gene. Journal of Bacteriology. 177(6):1452–1460, Mar. 1995.

Krautwurst et al. *Saccharomyces cerevisiae* phosphoenolpyruvate carboxykinase: revised amino acid sequence, site–directed mutagenesis, and microenvironment characteristics of cysteines 365 and 458. 34:6382–6388, 1995.

Alvear et al. ATP–dependent *Saccharomyces cerevisiae* phosphoenolpyruvate carboxykinase: isolation and suquence of a peptide containing a highly reactive cysteine. Biochimica et Biophysica Acta. 1119:35–38, 1992.

Medina et al. Sequence of the pckA gene of *Escherichia coli* K–12: relevance to genetic and allosteric regulation and homology of *E. coli* phosphoenolpyruvate carboxykinase with the enzymes from *Trypanosoma brucei* and *Saccharomyces cerevisiae*. Journal of, Dec. 1990.

Osteras et al. Site–directed mutagenesis and DNA sequence of pckA of Rhizobium NGR234, encoding phosphoenolpyruvate carboxykinase: gluconeogeneis and host–dependent symbiotic phenotype. Molecular General Genetics. 230:257–269, Nov. 1991.

Linss et al. Cloning and characterization of the gene encoding ATP–dependent phospho–enol–pyruvate carboxykinase in *Trypanosoma cruzi*: comparison of primary and predicted secondary structure with host GTP–dependent enzyme. 136:69–77, 1993.

Parsons et al. *Trypanosome glycosomal* protein P60 is homologous in Phosphoenolpyruvate carboxykinase (ATP). 17(15):6411, 1989.

Strucka et al. Nucleotide suquence of the phosphoenolpyruvate carboxykinase gene from *Saccharomyces cerevisiae*. Nucleic Acids Research. 16(22):10926, Nov. 1988.

Tada et al. Efficient gene introduction into rice by electroporation and analysis of transgenic plants: use of electroporation buffer lacking chloride ions. Theoretical and Applied Genetics. 80:475–480, 1990.

Hudspeth et al. Structure and expression of the maize gene encoding the phosphoenolpyruvate carboxykinase isozyme involved in C4 photosynthesis. Plant Molecular Biology, 12:579–589, 1989.

R. Hudspeth et al, "Structure and Expression of the Maize Gene Encoding the Phosphoenolpyruvate Carboxylase Isozyme Involved in C4 Photosynthesis", Plant Molecular Biology, vol. 12, 1989, pp. 579–589.

M. Matsuoka et al, "Expression of Photosynthetic Genes from the C4 Plant, Maize, in Tobacco", Mol. Gen. Genet. (1991), 225:411–419.

B. Martineau et al, "Expression of a $C_3$ Plant Rubisco SSU Gene in Regenerated $C_4$ Flaveria Plants", Plant Molecular Biology, vol. 13, 1989, pp. 419–426.

Chemical Abstract, M. Matsuoka et al, "Expression of Photosynthetic Genes from C4 Plant in C3 Plants" AN 119:218582 CA.

Derwent WPI English Abstract of Japanese Patent 4–222527.

Chih–ching, Plant Tissue Culture, Pitman Publishing Inc., pp. 43–51 (1981).

Kim et al, Plant Molecular Biology, vol. 26, pp. 423–434 (1994).

(List continued on next page.)

*Primary Examiner*—Douglas W. Robinson
*Assistant Examiner*—Thanda Wai
*Attorney, Agent, or Firm*—Birch, Stewart, Kolasch & Birch, LLP

[57] ABSTRACT

A cloned DNA encoding phosphoenolpyruvate carboxykinase of a $C_4$ plant is disclosed. The DNA according to the present invention encodes the amino acid sequence shown in SEQ ID NOS: 1–6 in Sequence Listing or the same amino acid sequence as shown in SEQ ID NOS: 1–6 except that one or more amino acid is added, deleted, inserted or substituted, with the proviso that the polypeptide having this amino acid sequence has phosphoenolpyruvate carboxykinase activity.

13 Claims, 3 Drawing Sheets

OTHER PUBLICATIONS

Finnegan et al, Plant Molecular Biology, vol. 27, pp. 365–376 (1995).
Yanisch–Perron et al, Gene, vol. 33, pp. 103–119 (1985).
Bilang et al, Gene, vol. 100, pp. 247–250 (1991).
Toriyama et al, Theor Appl Genet, vol. 73, pp. 16–19 (1986).
Hudspeth et al, Plant Molecular Biology, vol. 12, pp. 579–589 (1989).
Murashige et al, Physiologia Plantarum, vol. 15, pp. 473–497 (1962).
Sanger et al, Proc. Natl. Acad. Sci. USA, vol. 74, No. 12, pp. 5463–5467, (Dec. 1977).
Stucka eta al, Nucleic Acids Research, vol. 16, No. 22 (1988).
Komari et al, Theor Appl Genet, vol. 77, pp. 547–552 (1989).
Matsuoka et al, Plant Cell Physiol., vol. 29, No. 6, pp. 1015–1022 (1988).
Popot et al, Annu. Rev. Biophys. Biophys. Chem., vol. 19, pp. 369–403 (1990).
Ohira et al, Plant & Cell Physiol., vol. 14, pp. 1113–1121 (1973).
Chomczynski et al, Analytical Biochemistry, vol. 162, pp. 156–159 (1987).
Henikoff, Gene, vol. 28, pp. 351–359 (1984).
Burnell, Aust. J. Plant. Physiol., vol. 13, pp. 577–587 (1986).
Baba et al, Plant Cell Physiol., vol. 27, No. 3, pp. 463–471 (1986).
Tada et al, Theor Appl Genet, vol. 80, pp. 475–480 (1990).
Yie et al, Nucleic Acids Research, vol. 21, No. 2, p. 361 (1993).
Kyte et al, J. Mol. Biol., vol. 157, pp. 105–132 (1982).
Derwent WPI English Abstract of European Patent 504869.

```
  1' MASPNGGVTTYDYDDSDSAAPVRAQTIEELHSLQRKAAATAKDSASPLQSISASLASTAR
     *************.********.***************.*.**.************* **
  1" MASPNGGVTTYDYHDSDSAAPVNAQTIEELHSLQRKAATTTKDGASPLQSISASLASLAR

 61' EYGPNLVKGDPEA-KGAPPAPVKHQQ-AAAAAAIAASDSSLKFTHVLYNLSPAELYEQAF
     ************* *****.*.**** .****.***************************
 61" EYGPNLVKGDPEATKGAPPVPIKHQQPSAAAATIAASDSSLKFTHVLYNLSPAELYEQAF

119' GQKKSSFITSTGALATLSGAKTGRSPRDKRVVKDDTTAQELWWGKGSPNIEMDERQFVIN
     **********************************.**.**********************
121" GQKKSSFITSTGALATLSGAKTGRSPRDKRVVKDETTSQELWWGKGSPNIEMDERQFVIN

179' RERALDFLNSLDKVYVNDQFLNWDPENRIKVRIITSRAYHALFMHNMCIRPTEEELETFG
     ******.*****************.********************************.**
181" RERALDYLNSLDKVYVNDQFLNWDSENRIKVRIITSRAYHALFMHNMCIRPTEEELESFG

239' TPDFTIYNAGEFPANRYANYMTSSTSINISLARREMVILGTQYAGEMKKGLFGVMHYLMP
     ************************************************************
241" TPDFTIYNAGEFPANRYANYMTSSTSINISLARREMVILGTQYAGEMKKGLFGVMHYLMP

299' KRGILSLHSGCNMGKEGDVALFFGLSGTGKTTLSTDHNRLLIGDDEHCWSDNGVSNIEGG
     ************************************************************
301" KRGILSLHSGCNMGKEGDVALFFGLSGTGKTTLSTDHNRLLIGDDEHCWSDNGVSNIEGG

359' CYAKCIDLSKEKEPDIWNAITFGTVLENVVFNERTREVDYADKSITENTRAAYPIEFIPN
     *********.**********.***************************************
361" CYAKCIDLSQEKEPDIWNAIKFGTVLENVVFNERTREVDYADKSITENTRAAYPIEFIPN

419' AKIPCVGPHPKNVILLACDAYGVLPPVSKLNLAQTMYHFISGYTAIVAGTEDGVKEPTAT
     ************************************************************
421" AKIPCVGPHPKNVILLACDAYGVLPPVSKLNLAQTMYHFISGYTAIVAGTEDGVKEPTAT

479' FSACFGAAFIMYHPTKYAAMLAEKMQKYGRTGWLVNTGWSGGRYGVGNRIKLPYTRKIID
     ***************************** ******************************
481" FSACFGAAFIMYHPTKYAAMLAEKMQKYGATGWLVNTGWSGGRYGVGNRIKLPYTRKIID

539' AIHSGELLTANYKKTEVFGLEIPTEINGVPSEILDPVNTWTDKAAYKETLLKLAGLFKNN
     ********.*.*************.***********************************
541" AIHSGELLNASYKKTEVFGLEIPTAINGVPSEILDPVNTWTDKAAYKETLLKLAGLFKNN

599' FEVFASYKIGDDNSLTEQILAAGPNF
     **********..**********.***
601" FEVFASYKIGNNNSLTEQILAAAPNF
```

Fig. 3

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 2220 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 58..1929

( x i ) SEQUENCE DESCRIPTION: SEQ ID NO:1:

```
CTCCACACCG CTTCCTCGGC GGCCGGCGCA CGTCGCTGCT CCCGACGCTC GAACGAG          57

ATG GCG TCG CCG AAC GGT GGT GTC ACG ACC TAT GAC TAC GAC GAC AGC        105
Met Ala Ser Pro Asn Gly Gly Val Thr Thr Tyr Asp Tyr Asp Asp Ser
  1               5                  10                  15

GAC AGC GCG GCG CCG GTG CGC GCG CAG ACC ATC GAG GAG CTG CAT TCG        153
Asp Ser Ala Ala Pro Val Arg Ala Gln Thr Ile Glu Glu Leu His Ser
             20                  25                  30

CTG CAG CGG AAG GCT GCC GCC ACG GCC AAG GAT AGC GCA TCG CCC CTG        201
Leu Gln Arg Lys Ala Ala Ala Thr Ala Lys Asp Ser Ala Ser Pro Leu
         35                  40                  45

CAG TCC ATC AGC GCG TCA TTG GCG TCT ACG GCA CGT GAA TAT GGC CCC        249
Gln Ser Ile Ser Ala Ser Leu Ala Ser Thr Ala Arg Glu Tyr Gly Pro
     50                  55                  60

AAC CTC GTC AAG GGT GAC CCG GAA GCG AAG GGC GCG CCG CCG GCG CCG        297
Asn Leu Val Lys Gly Asp Pro Glu Ala Lys Gly Ala Pro Pro Ala Pro
 65                  70                  75                  80

GTA AAG CAC CAG CAG GCC GCC GCC GCT GCC GCC ATC GCC GCC AGT GAC        345
Val Lys His Gln Gln Ala Ala Ala Ala Ala Ala Ile Ala Ala Ser Asp
                 85                  90                  95

AGC TCC CTC AAG TTC ACC CAT GTC CTC TAC AAC CTC TCC CCC GCT GAG        393
Ser Ser Leu Lys Phe Thr His Val Leu Tyr Asn Leu Ser Pro Ala Glu
            100                 105                 110

CTG TAC GAG CAG GCT TTC GGG CAA AAG AAG AGT TCG TTC ATC ACG TCG        441
Leu Tyr Glu Gln Ala Phe Gly Gln Lys Lys Ser Ser Phe Ile Thr Ser
        115                 120                 125

ACC GGC GCG CTG GCC ACG CTG TCC GGC GCC AAG ACC GGT CGG TCG CCC        489
Thr Gly Ala Leu Ala Thr Leu Ser Gly Ala Lys Thr Gly Arg Ser Pro
    130                 135                 140

AGG GAC AAG CGC GTC GTC AAG GAC GAC ACC ACC GCG CAG GAG CTG TGG        537
Arg Asp Lys Arg Val Val Lys Asp Asp Thr Thr Ala Gln Glu Leu Trp
145                 150                 155                 160

TGG GGC AAG GGC TCG CCC AAC ATC GAG ATG GAC GAG CGC CAG TTC GTG        585
Trp Gly Lys Gly Ser Pro Asn Ile Glu Met Asp Glu Arg Gln Phe Val
                165                 170                 175

ATC AAC AGG GAG CGG GCC CTG GAC TTC CTC AAC TCC CTG GAC AAG GTG        633
Ile Asn Arg Glu Arg Ala Leu Asp Phe Leu Asn Ser Leu Asp Lys Val
            180                 185                 190

TAC GTC AAC GAC CAG TTC CTC AAC TGG GAC CCC GAG AAC CGC ATC AAG        681
Tyr Val Asn Asp Gln Phe Leu Asn Trp Asp Pro Glu Asn Arg Ile Lys
        195                 200                 205

GTC CGG ATC ATC ACC TCC AGG GCG TAC CAC GCC CTC TTC ATG CAC AAC        729
Val Arg Ile Ile Thr Ser Arg Ala Tyr His Ala Leu Phe Met His Asn
```

-continued

```
    210                           215                           220

ATG TGC ATC CGT CCC ACC GAG GAG GAG CTG GAG ACC TTC GGC ACG CCG       777
Met Cys Ile Arg Pro Thr Glu Glu Glu Leu Glu Thr Phe Gly Thr Pro
225                     230                     235                 240

GAC TTC ACC ATT TAC AAC GCC GGG GAG TTC CCC GCC AAC CGT TAC GCC       825
Asp Phe Thr Ile Tyr Asn Ala Gly Glu Phe Pro Ala Asn Arg Tyr Ala
                245                     250                     255

AAC TAC ATG ACG TCG TCG ACG AGC ATA AAC ATC AGC CTC GCT AGG AGG       873
Asn Tyr Met Thr Ser Ser Thr Ser Ile Asn Ile Ser Leu Ala Arg Arg
            260                     265                     270

GAG ATG GTG ATC CTG GGC ACG CAG TAC GCT GGG GAG ATG AAG AAG GGC       921
Glu Met Val Ile Leu Gly Thr Gln Tyr Ala Gly Glu Met Lys Lys Gly
        275                     280                     285

CTC TTC GGC GTC ATG CAC TAC CTC ATG CCC AAG CGC GGC ATC CTC TCG       969
Leu Phe Gly Val Met His Tyr Leu Met Pro Lys Arg Gly Ile Leu Ser
    290                     295                     300

CTG CAC TCC GGG TGC AAC ATG GGC AAG GAA GGT GAC GTC GCC CTC TTC      1017
Leu His Ser Gly Cys Asn Met Gly Lys Glu Gly Asp Val Ala Leu Phe
305                     310                     315                 320

TTC GGG CTC TCA GGT ACC GGG AAG ACG ACG CTG TCA ACT GAC CAC AAC      1065
Phe Gly Leu Ser Gly Thr Gly Lys Thr Thr Leu Ser Thr Asp His Asn
                325                     330                     335

AGG CTC CTG ATC GGT GAT GAC GAG CAC TGC TGG AGC GAC AAT GGC GTC      1113
Arg Leu Leu Ile Gly Asp Asp Glu His Cys Trp Ser Asp Asn Gly Val
            340                     345                     350

TCC AAC ATT GAG GGA GGT TGC TAT GCC AAG TGC ATC GAC CTG TCC AAG      1161
Ser Asn Ile Glu Gly Gly Cys Tyr Ala Lys Cys Ile Asp Leu Ser Lys
        355                     360                     365

GAG AAA GAA CCT GAT ATC TGG AAC GCC ATC ACG TTT GGA ACA GTG CTG      1209
Glu Lys Glu Pro Asp Ile Trp Asn Ala Ile Thr Phe Gly Thr Val Leu
    370                     375                     380

GAA AAC GTC GTC TTC AAC GAG CGC ACT CGT GAA GTT GAC TAC GCC GAC      1257
Glu Asn Val Val Phe Asn Glu Arg Thr Arg Glu Val Asp Tyr Ala Asp
385                     390                     395                 400

AAA TCT ATC ACC GAG AAC ACC CGG GCC GCC TAC CCG ATC GAG TTC ATC      1305
Lys Ser Ile Thr Glu Asn Thr Arg Ala Ala Tyr Pro Ile Glu Phe Ile
                405                     410                     415

CCC AAC GCC AAG ATC CCA TGC GTC GGG CCG CAC CCC AAG AAC GTC ATC      1353
Pro Asn Ala Lys Ile Pro Cys Val Gly Pro His Pro Lys Asn Val Ile
            420                     425                     430

CTC CTG GCC TGC GAC GCG TAC GGC GTG CTC CCG CCG GTG AGC AAG CTC      1401
Leu Leu Ala Cys Asp Ala Tyr Gly Val Leu Pro Pro Val Ser Lys Leu
        435                     440                     445

AAC CTG GCG CAG ACC ATG TAC CAC TTC ATC AGC GGC TAC ACT GCC ATC      1449
Asn Leu Ala Gln Thr Met Tyr His Phe Ile Ser Gly Tyr Thr Ala Ile
    450                     455                     460

GTC GCC GGC ACG GAG GAC GGC GTC AAG GAG CCG ACG GCG ACC TTC TCG      1497
Val Ala Gly Thr Glu Asp Gly Val Lys Glu Pro Thr Ala Thr Phe Ser
465                     470                     475                 480

GCC TGC TTC GGC GCG GCC TTC ATC ATG TAC CAC CCC ACC AAG TAC GCC      1545
Ala Cys Phe Gly Ala Ala Phe Ile Met Tyr His Pro Thr Lys Tyr Ala
                485                     490                     495

GCC ATG CTC GCC GAG AAG ATG CAG AAG TAC GGC CGC ACC GGG TGG CTT      1593
Ala Met Leu Ala Glu Lys Met Gln Lys Tyr Gly Arg Thr Gly Trp Leu
            500                     505                     510

GTC AAC ACC GGC TGG TCC GGC GGC AGG TAC GGT GTG GGC AAC AGG ATC      1641
Val Asn Thr Gly Trp Ser Gly Gly Arg Tyr Gly Val Gly Asn Arg Ile
        515                     520                     525

AAG CTG CCG TAC ACC AGG AAG ATC ATC GAC GCC ATC CAC TCC GGC GAG      1689
Lys Leu Pro Tyr Thr Arg Lys Ile Ile Asp Ala Ile His Ser Gly Glu
```

```
                    530                                 535                                 540

CTC CTC ACC GCC AAC TAC AAG AAG ACC GAG GTG TTC GGG CTG GAG ATC    1737
Leu Leu Thr Ala Asn Tyr Lys Lys Thr Glu Val Phe Gly Leu Glu Ile
545                 550                 555                 560

CCC ACC GAG ATC AAC GGC GTG CCG TCG GAA ATC CTC GAC CCC GTC AAC    1785
Pro Thr Glu Ile Asn Gly Val Pro Ser Glu Ile Leu Asp Pro Val Asn
                565                 570                 575

ACC TGG ACG GAC AAG GCC GCG TAC AAG GAG ACT CTC CTG AAG CTT GCC    1833
Thr Trp Thr Asp Lys Ala Ala Tyr Lys Glu Thr Leu Leu Lys Leu Ala
            580                 585                 590

GGG CTC TTC AAG AAC AAC TTC GAG GTG TTC GCC AGC TAC AAG ATC GGG    1881
Gly Leu Phe Lys Asn Asn Phe Glu Val Phe Ala Ser Tyr Lys Ile Gly
        595                 600                 605

GAC GAC AAC AGC CTG ACC GAA CAG ATC CTT GCC GCA GGC CCC AAC TTC    1929
Asp Asp Asn Ser Leu Thr Glu Gln Ile Leu Ala Ala Gly Pro Asn Phe
    610                 615                 620

TGATTCCAAG CAATGGATCC GGAACGGCGA GGCGTTGGAG TTGGTTCAGA ATGAACCAGT    1989

GGTGCGTGTG TGCGTGCGTG TGTTACGATG ATGATGATGA TGGCGAAAAA AAAACTGTTG    2049

GACTGATGAT GTGCCAACAT GGAGTAGACC AGCTCTGTAT GCTATCATGT GTGTGTGGTG    2109

TTGTTACCTG TGGTTTGTTC TATCTGGGCG TGGTCCTGGT GTAAATCTGT ATGCCTGTTC    2169

GGCGGCCTGG TCCTGGTGTA AATCTGGGCG TGCTTTGCAT CTTGCCCGTG T             2220
```

( 2 ) INFORMATION FOR SEQ ID NO:2:

( i ) SEQUENCE CHARACTERISTICS:
( A ) LENGTH: 624 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Ala Ser Pro Asn Gly Gly Val Thr Thr Tyr Asp Tyr Asp Asp Ser
 1               5                  10                  15

Asp Ser Ala Ala Pro Val Arg Ala Gln Thr Ile Glu Glu Leu His Ser
            20                  25                  30

Leu Gln Arg Lys Ala Ala Ala Thr Ala Lys Asp Ser Ala Ser Pro Leu
        35                  40                  45

Gln Ser Ile Ser Ala Ser Leu Ala Ser Thr Ala Arg Glu Tyr Gly Pro
    50                  55                  60

Asn Leu Val Lys Gly Asp Pro Glu Ala Lys Gly Ala Pro Pro Ala Pro
 65                 70                  75                  80

Val Lys His Gln Gln Ala Ala Ala Ala Ala Ala Ile Ala Ala Ser Asp
                85                  90                  95

Ser Ser Leu Lys Phe Thr His Val Leu Tyr Asn Leu Ser Pro Ala Glu
            100                 105                 110

Leu Tyr Glu Gln Ala Phe Gly Gln Lys Lys Ser Ser Phe Ile Thr Ser
        115                 120                 125

Thr Gly Ala Leu Ala Thr Leu Ser Gly Ala Lys Thr Gly Arg Ser Pro
    130                 135                 140

Arg Asp Lys Arg Val Val Lys Asp Asp Thr Thr Ala Gln Glu Leu Trp
145                 150                 155                 160

Trp Gly Lys Gly Ser Pro Asn Ile Glu Met Asp Glu Arg Gln Phe Val
                165                 170                 175

Ile Asn Arg Glu Arg Ala Leu Asp Phe Leu Asn Ser Leu Asp Lys Val
            180                 185                 190
```

-continued

Tyr Val Asn Asp Gln Phe Leu Asn Trp Asp Pro Glu Asn Arg Ile Lys
        195                 200                 205

Val Arg Ile Ile Thr Ser Arg Ala Tyr His Ala Leu Phe Met His Asn
    210                 215                 220

Met Cys Ile Arg Pro Thr Glu Glu Glu Leu Glu Thr Phe Gly Thr Pro
225                 230                 235                 240

Asp Phe Thr Ile Tyr Asn Ala Gly Glu Phe Pro Ala Asn Arg Tyr Ala
                245                 250                 255

Asn Tyr Met Thr Ser Ser Thr Ser Ile Asn Ile Ser Leu Ala Arg Arg
            260                 265                 270

Glu Met Val Ile Leu Gly Thr Gln Tyr Ala Gly Glu Met Lys Lys Gly
        275                 280                 285

Leu Phe Gly Val Met His Tyr Leu Met Pro Lys Arg Gly Ile Leu Ser
    290                 295                 300

Leu His Ser Gly Cys Asn Met Gly Lys Glu Gly Asp Val Ala Leu Phe
305                 310                 315                 320

Phe Gly Leu Ser Gly Thr Gly Lys Thr Thr Leu Ser Thr Asp His Asn
                325                 330                 335

Arg Leu Leu Ile Gly Asp Asp Glu His Cys Trp Ser Asp Asn Gly Val
            340                 345                 350

Ser Asn Ile Glu Gly Gly Cys Tyr Ala Lys Cys Ile Asp Leu Ser Lys
        355                 360                 365

Glu Lys Glu Pro Asp Ile Trp Asn Ala Ile Thr Phe Gly Thr Val Leu
    370                 375                 380

Glu Asn Val Val Phe Asn Glu Arg Thr Arg Glu Val Asp Tyr Ala Asp
385                 390                 395                 400

Lys Ser Ile Thr Glu Asn Thr Arg Ala Ala Tyr Pro Ile Glu Phe Ile
                405                 410                 415

Pro Asn Ala Lys Ile Pro Cys Val Gly Pro His Pro Lys Asn Val Ile
            420                 425                 430

Leu Leu Ala Cys Asp Ala Tyr Gly Val Leu Pro Pro Val Ser Lys Leu
        435                 440                 445

Asn Leu Ala Gln Thr Met Tyr His Phe Ile Ser Gly Tyr Thr Ala Ile
    450                 455                 460

Val Ala Gly Thr Glu Asp Gly Val Lys Glu Pro Thr Ala Thr Phe Ser
465                 470                 475                 480

Ala Cys Phe Gly Ala Ala Phe Ile Met Tyr His Pro Thr Lys Tyr Ala
                485                 490                 495

Ala Met Leu Ala Glu Lys Met Gln Lys Tyr Gly Arg Thr Gly Trp Leu
            500                 505                 510

Val Asn Thr Gly Trp Ser Gly Gly Arg Tyr Gly Val Gly Asn Arg Ile
        515                 520                 525

Lys Leu Pro Tyr Thr Arg Lys Ile Ile Asp Ala Ile His Ser Gly Glu
    530                 535                 540

Leu Leu Thr Ala Asn Tyr Lys Lys Thr Glu Val Phe Gly Leu Glu Ile
545                 550                 555                 560

Pro Thr Glu Ile Asn Gly Val Pro Ser Glu Ile Leu Asp Pro Val Asn
                565                 570                 575

Thr Trp Thr Asp Lys Ala Ala Tyr Lys Glu Thr Leu Leu Lys Leu Ala
            580                 585                 590

Gly Leu Phe Lys Asn Asn Phe Glu Val Phe Ala Ser Tyr Lys Ile Gly
        595                 600                 605

Asp Asp Asn Ser Leu Thr Glu Gln Ile Leu Ala Ala Gly Pro Asn Phe
    610                 615                 620

( 2 ) INFORMATION FOR SEQ ID NO:3:

( i ) SEQUENCE CHARACTERISTICS:
( A ) LENGTH: 2245 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 45..1922

( x i ) SEQUENCE DESCRIPTION: SEQ ID NO:3:

```
CCTCGGCGGC CGGCGCACGT CGCTGCTCCC GACGCTCGAA CGAG ATG GCG TCG CCG      56
                                                 Met Ala Ser Pro
                                                 625

AAC GGT GGT GTC ACG ACC TAC GAC TAC CAC GAC AGC GAC AGC GCG GCG      104
Asn Gly Gly Val Thr Thr Tyr Asp Tyr His Asp Ser Asp Ser Ala Ala
    630                 635                 640

CCG GTG AAC GCG CAG ACC ATC GAA GAG CTG CAT TCG CTG CAG CGG AAG      152
Pro Val Asn Ala Gln Thr Ile Glu Glu Leu His Ser Leu Gln Arg Lys
645                 650                 655                 660

GCT GCC ACC ACG ACC AAG GAT GGC GCA TCG CCC CTG CAG TCC ATC AGC      200
Ala Ala Thr Thr Thr Lys Asp Gly Ala Ser Pro Leu Gln Ser Ile Ser
                665                 670                 675

GCG TCA TTG GCG TCT CTG GCA CGT GAA TAT GGC CCC AAC CTC GTC AAG      248
Ala Ser Leu Ala Ser Leu Ala Arg Glu Tyr Gly Pro Asn Leu Val Lys
            680                 685                 690

GGT GAC CCG GAA GCG ACC AAG GGC GCG CCG CCG GTG CCG ATA AAG CAC      296
Gly Asp Pro Glu Ala Thr Lys Gly Ala Pro Pro Val Pro Ile Lys His
        695                 700                 705

CAG CAG CCC TCC GCC GCC GCT GCC ACC ATC GCC GCC AGC GAC AGC TCC      344
Gln Gln Pro Ser Ala Ala Ala Ala Thr Ile Ala Ala Ser Asp Ser Ser
    710                 715                 720

CTC AAG TTC ACC CAT GTC CTC TAC AAC CTC TCC CCC GCT GAG TTG TAC      392
Leu Lys Phe Thr His Val Leu Tyr Asn Leu Ser Pro Ala Glu Leu Tyr
725                 730                 735                 740

GAG CAG GCT TTC GGC CAA AAG AAG AGT TCG TTC ATC ACG TCG ACC GGC      440
Glu Gln Ala Phe Gly Gln Lys Lys Ser Ser Phe Ile Thr Ser Thr Gly
                745                 750                 755

GCG CTG GCC ACG CTG TCC GGC GCC AAG ACC GGC CGG TCG CCC AGG GAC      488
Ala Leu Ala Thr Leu Ser Gly Ala Lys Thr Gly Arg Ser Pro Arg Asp
            760                 765                 770

AAG CGT GTC GTC AAG GAC GAG ACC ACC TCA CAG GAG CTC TGG TGG GGC      536
Lys Arg Val Val Lys Asp Glu Thr Thr Ser Gln Glu Leu Trp Trp Gly
        775                 780                 785

AAG GGC TCG CCC AAC ATC GAG ATG GAC GAG CGC CAG TTC GTG ATC AAC      584
Lys Gly Ser Pro Asn Ile Glu Met Asp Glu Arg Gln Phe Val Ile Asn
    790                 795                 800

AGG GAG CGG GCC CTG GAC TAC CTC AAC TCA CTG GAC AAG GTG TAC GTC      632
Arg Glu Arg Ala Leu Asp Tyr Leu Asn Ser Leu Asp Lys Val Tyr Val
805                 810                 815                 820

AAC GAC CAG TTC CTC AAC TGG GAC TCG GAG AAC CGC ATC AAG GTC CGC      680
Asn Asp Gln Phe Leu Asn Trp Asp Ser Glu Asn Arg Ile Lys Val Arg
                825                 830                 835

ATC ATC ACC TCC AGG GCG TAC CAC GCC CTC TTT ATG CAC AAC ATG TGC      728
Ile Ile Thr Ser Arg Ala Tyr His Ala Leu Phe Met His Asn Met Cys
            840                 845                 850

ATC CGG CCC ACG GAA GAG GAG CTG GAG AGC TTC GGC ACG CCG GAC TTC      776
Ile Arg Pro Thr Glu Glu Glu Leu Glu Ser Phe Gly Thr Pro Asp Phe
```

-continued

```
          855                      860                      865

ACC ATT TAC AAC GCC GGG GAG TTC CCC GCC AAC CGT TAC GCC AAC TAC     824
Thr Ile Tyr Asn Ala Gly Glu Phe Pro Ala Asn Arg Tyr Ala Asn Tyr
    870                     875                     880

ATG ACG TCG TCG ACG AGC ATA AAC ATC AGC CTC GCT AGG AGG GAG ATG     872
Met Thr Ser Ser Thr Ser Ile Asn Ile Ser Leu Ala Arg Arg Glu Met
885                     890                     895                 900

GTA ATC CTG GGC ACG CAG TAC GCC GGG GAG ATG AAG AAG GGG CTC TTT     920
Val Ile Leu Gly Thr Gln Tyr Ala Gly Glu Met Lys Lys Gly Leu Phe
                905                     910                     915

GGC GTC ATG CAC TAC CTC ATG CCC AAG CGA GGC ATC CTC TCG CTG CAC     968
Gly Val Met His Tyr Leu Met Pro Lys Arg Gly Ile Leu Ser Leu His
            920                     925                     930

TCC GGG TGC AAC ATG GGC AAG GAG GGT GAC GTC GCC CTC TTC TTT GGG    1016
Ser Gly Cys Asn Met Gly Lys Glu Gly Asp Val Ala Leu Phe Phe Gly
        935                     940                     945

CTC TCA GGT ACC GGG AAG ACG ACG CTG TCA ACT GAC CAC AAT AGG CTC    1064
Leu Ser Gly Thr Gly Lys Thr Thr Leu Ser Thr Asp His Asn Arg Leu
    950                     955                     960

CTG ATC GGT GAT GAC GAG CAC TGC TGG AGC GAC AAT GGC GTC TCC AAC    1112
Leu Ile Gly Asp Asp Glu His Cys Trp Ser Asp Asn Gly Val Ser Asn
965                     970                     975                 980

ATT GAG GGA GGT TGC TAT GCC AAG TGC ATT GAC CTG TCC CAG GAG AAG    1160
Ile Glu Gly Gly Cys Tyr Ala Lys Cys Ile Asp Leu Ser Gln Glu Lys
                985                     990                     995

GAA CCT GAT ATC TGG AAC GCC ATC AAG TTT GGA ACT GTG CTG GAG AAC    1208
Glu Pro Asp Ile Trp Asn Ala Ile Lys Phe Gly Thr Val Leu Glu Asn
            1000                    1005                    1010

GTC GTC TTC AAC GAG CGC ACT CGT GAA GTT GAC TAC GCC GAC AAA TCT    1256
Val Val Phe Asn Glu Arg Thr Arg Glu Val Asp Tyr Ala Asp Lys Ser
        1015                    1020                    1025

ATC ACC GAG AAC ACC CGG GCC GCC TAC CCG ATC GAG TTC ATC CCC AAC    1304
Ile Thr Glu Asn Thr Arg Ala Ala Tyr Pro Ile Glu Phe Ile Pro Asn
    1030                    1035                    1040

GCC AAG ATC CCG TGC GTC GGG CCG CAC CCC AAG AAC GTC ATC CTC CTG    1352
Ala Lys Ile Pro Cys Val Gly Pro His Pro Lys Asn Val Ile Leu Leu
1045                    1050                    1055                1060

GCG TGC GAC GCG TAC GGC GTG CTC CCG CCG GTG AGC AAG CTC AAC CTG    1400
Ala Cys Asp Ala Tyr Gly Val Leu Pro Pro Val Ser Lys Leu Asn Leu
                1065                    1070                    1075

GCG CAG ACC ATG TAC CAC TTC ATC AGC GGC TAC ACC GCC ATC GTC GCC    1448
Ala Gln Thr Met Tyr His Phe Ile Ser Gly Tyr Thr Ala Ile Val Ala
            1080                    1085                    1090

GGC ACA GAG GAC GGC GTC AAG GAG CCG ACG GCC ACA TTC TCG GCC TGC    1496
Gly Thr Glu Asp Gly Val Lys Glu Pro Thr Ala Thr Phe Ser Ala Cys
        1095                    1100                    1105

TTC GGC GCG GCC TTC ATC ATG TAC CAC CCC ACC AAG TAC GCA GCC ATG    1544
Phe Gly Ala Ala Phe Ile Met Tyr His Pro Thr Lys Tyr Ala Ala Met
    1110                    1115                    1120

CTC GCC GAG AAG ATG CAG AAG TAC GGC GCC ACC GGG TGG CTT GTC AAC    1592
Leu Ala Glu Lys Met Gln Lys Tyr Gly Ala Thr Gly Trp Leu Val Asn
1125                    1130                    1135                1140

ACT GGC TGG TCC GGC GGC AGG TAC GGT GTG GGC AAC AGG ATC AAG CTG    1640
Thr Gly Trp Ser Gly Gly Arg Tyr Gly Val Gly Asn Arg Ile Lys Leu
                1145                    1150                    1155

CCG TAC ACC AGG AAG ATC ATC GAC GCC ATC CAC TCC GGC GAG CTC CTC    1688
Pro Tyr Thr Arg Lys Ile Ile Asp Ala Ile His Ser Gly Glu Leu Leu
            1160                    1165                    1170

AAC GCC AGC TAC AAG AAG ACC GAG GTG TTC GGG CTG GAG ATC CCC ACC    1736
Asn Ala Ser Tyr Lys Lys Thr Glu Val Phe Gly Leu Glu Ile Pro Thr
```

```
        1175                    1180                    1185

GCG ATC AAC GGC GTG CCG TCG GAA ATT CTC GAC CCC GTC AAC ACC TGG      1784
Ala Ile Asn Gly Val Pro Ser Glu Ile Leu Asp Pro Val Asn Thr Trp
    1190                    1195                    1200

ACG GAC AAG GCC GCG TAC AAG GAG ACG CTC CTG AAG CTT GCC GGG CTC      1832
Thr Asp Lys Ala Ala Tyr Lys Glu Thr Leu Leu Lys Leu Ala Gly Leu
1205                    1210                    1215                    1220

TTC AAG AAC AAC TTC GAG GTG TTC GCC AGC TAC AAG ATC GGG AAC AAC      1880
Phe Lys Asn Asn Phe Glu Val Phe Ala Ser Tyr Lys Ile Gly Asn Asn
                1225                    1230                    1235

AAC AGC CTG ACA GAA CAG ATC CTC GCC GCA GCG CCC AAC TTC              1922
Asn Ser Leu Thr Glu Gln Ile Leu Ala Ala Ala Pro Asn Phe
            1240                    1245                    1250

TGATTCCAAG CAATGGATCT GGAACGGCGA GGCGATGGAG TTGGTTCAGA ATAAACCGGT    1982

GGTGCGTGCG TGCGTGTGTT ACGATGATGA TGATGGCAAA AAAAAAAACT GTTGGACTGA    2042

TTATGTGCCA ACATGCAGTA GACCAGCTCT GTATGCTATC ATGTGTGTGT GGTGGTGTTA    2102

CCTGTAAGGT TTGTTCTATC AGCTGGTTCG GCGGCCTGGT TCTGGTGTAA ATCTGGGCGT    2162

GCTTTGCATC TTGCCCGTGT ATTCCCTCTT GTTTCAGAAT TTGAATATAT ACTATCTTAT    2222

TTCCAAAAAA AAAAAAAAAA AAA                                            2245
```

( 2 ) INFORMATION FOR SEQ ID NO:4:

( i ) SEQUENCE CHARACTERISTICS:
( A ) LENGTH: 626 amino acids
( B ) TYPE: amino acid
( D ) TOPOLOGY: linear ( i i ) MOLECULE TYPE: protein ( x i ) SEQUENCE DESCRIPTION: SEQ ID NO:4:

```
Met Ala Ser Pro Asn Gly Gly Val Thr Thr Tyr Asp Tyr His Asp Ser
  1               5                  10                  15

Asp Ser Ala Ala Pro Val Asn Ala Gln Thr Ile Glu Glu Leu His Ser
             20                  25                  30

Leu Gln Arg Lys Ala Ala Thr Thr Thr Lys Asp Gly Ala Ser Pro Leu
         35                  40                  45

Gln Ser Ile Ser Ala Ser Leu Ala Ser Leu Ala Arg Glu Tyr Gly Pro
     50                  55                  60

Asn Leu Val Lys Gly Asp Pro Glu Ala Thr Lys Gly Ala Pro Pro Val
 65                  70                  75                  80

Pro Ile Lys His Gln Gln Pro Ser Ala Ala Ala Ala Thr Ile Ala Ala
                 85                  90                  95

Ser Asp Ser Ser Leu Lys Phe Thr His Val Leu Tyr Asn Leu Ser Pro
            100                 105                 110

Ala Glu Leu Tyr Glu Gln Ala Phe Gly Gln Lys Lys Ser Ser Phe Ile
        115                 120                 125

Thr Ser Thr Gly Ala Leu Ala Thr Leu Ser Gly Ala Lys Thr Gly Arg
    130                 135                 140

Ser Pro Arg Asp Lys Arg Val Val Lys Asp Glu Thr Thr Ser Gln Glu
145                 150                 155                 160

Leu Trp Trp Gly Lys Gly Ser Pro Asn Ile Glu Met Asp Glu Arg Gln
                165                 170                 175

Phe Val Ile Asn Arg Glu Arg Ala Leu Asp Tyr Leu Asn Ser Leu Asp
            180                 185                 190

Lys Val Tyr Val Asn Asp Gln Phe Leu Asn Trp Asp Ser Glu Asn Arg
        195                 200                 205
```

```
Ile Lys Val Arg Ile Ile Thr Ser Arg Ala Tyr His Ala Leu Phe Met
    210                 215                 220

His Asn Met Cys Ile Arg Pro Thr Glu Glu Glu Leu Glu Ser Phe Gly
225                 230                 235                 240

Thr Pro Asp Phe Thr Ile Tyr Asn Ala Gly Glu Phe Pro Ala Asn Arg
                245                 250                 255

Tyr Ala Asn Tyr Met Thr Ser Ser Thr Ser Ile Asn Ile Ser Leu Ala
            260                 265                 270

Arg Arg Glu Met Val Ile Leu Gly Thr Gln Tyr Ala Gly Glu Met Lys
        275                 280                 285

Lys Gly Leu Phe Gly Val Met His Tyr Leu Met Pro Lys Arg Gly Ile
    290                 295                 300

Leu Ser Leu His Ser Gly Cys Asn Met Gly Lys Glu Gly Asp Val Ala
305                 310                 315                 320

Leu Phe Phe Gly Leu Ser Gly Thr Gly Lys Thr Thr Leu Ser Thr Asp
                325                 330                 335

His Asn Arg Leu Leu Ile Gly Asp Asp Glu His Cys Trp Ser Asp Asn
            340                 345                 350

Gly Val Ser Asn Ile Glu Gly Gly Cys Tyr Ala Lys Cys Ile Asp Leu
        355                 360                 365

Ser Gln Glu Lys Glu Pro Asp Ile Trp Asn Ala Ile Lys Phe Gly Thr
    370                 375                 380

Val Leu Glu Asn Val Val Phe Asn Glu Arg Thr Arg Glu Val Asp Tyr
385                 390                 395                 400

Ala Asp Lys Ser Ile Thr Glu Asn Thr Arg Ala Ala Tyr Pro Ile Glu
                405                 410                 415

Phe Ile Pro Asn Ala Lys Ile Pro Cys Val Gly Pro His Pro Lys Asn
            420                 425                 430

Val Ile Leu Leu Ala Cys Asp Ala Tyr Gly Val Leu Pro Pro Val Ser
        435                 440                 445

Lys Leu Asn Leu Ala Gln Thr Met Tyr His Phe Ile Ser Gly Tyr Thr
    450                 455                 460

Ala Ile Val Ala Gly Thr Glu Asp Gly Val Lys Glu Pro Thr Ala Thr
465                 470                 475                 480

Phe Ser Ala Cys Phe Gly Ala Ala Phe Ile Met Tyr His Pro Thr Lys
                485                 490                 495

Tyr Ala Ala Met Leu Ala Glu Lys Met Gln Lys Tyr Gly Ala Thr Gly
            500                 505                 510

Trp Leu Val Asn Thr Gly Trp Ser Gly Gly Arg Tyr Gly Val Gly Asn
        515                 520                 525

Arg Ile Lys Leu Pro Tyr Thr Arg Lys Ile Ile Asp Ala Ile His Ser
    530                 535                 540

Gly Glu Leu Leu Asn Ala Ser Tyr Lys Lys Thr Glu Val Phe Gly Leu
545                 550                 555                 560

Glu Ile Pro Thr Ala Ile Asn Gly Val Pro Ser Glu Ile Leu Asp Pro
                565                 570                 575

Val Asn Thr Trp Thr Asp Lys Ala Ala Tyr Lys Glu Thr Leu Leu Lys
            580                 585                 590

Leu Ala Gly Leu Phe Lys Asn Asn Phe Glu Val Phe Ala Ser Tyr Lys
        595                 600                 605

Ile Gly Asn Asn Asn Ser Leu Thr Glu Gln Ile Leu Ala Ala Ala Pro
    610                 615                 620

Asn Phe
```

625

( 2 ) INFORMATION FOR SEQ ID NO:5:

( i ) SEQUENCE CHARACTERISTICS:
( A ) LENGTH: 2109 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..1863

( x i ) SEQUENCE DESCRIPTION: SEQ ID NO:5:

ATG GCC CCC TCC GTG ATG GCG TCG TCG GCC ACC ACC GTC GCT CCC TTC 48
Met Ala Pro Ser Val Met Ala Ser Ser Ala Thr Thr Val Ala Pro Phe
630 635 640

CAG GGG CTC AAG TCC ACC GCC GGC ATG CCC GTC GCC CGC CGC TCC GGC 96
Gln Gly Leu Lys Ser Thr Ala Gly Met Pro Val Ala Arg Arg Ser Gly
645 650 655

AAC TCC AGC TTC GGC AAC GTC AGC AAT GGC GGC AGG ATC AGG TGC ATG 144
Asn Ser Ser Phe Gly Asn Val Ser Asn Gly Gly Arg Ile Arg Cys Met
660 665 670

CAG TCT AGA TCT CTG GCA CGT GAA TAT GGC CCC AAC CTC GTC AAG GGT 192
Gln Ser Arg Ser Leu Ala Arg Glu Tyr Gly Pro Asn Leu Val Lys Gly
675 680 685 690

GAC CCG GAA GCG ACC AAG GGC GCG CCG CCG GTG CCG ATA AAG CAC CAG 240
Asp Pro Glu Ala Thr Lys Gly Ala Pro Pro Val Pro Ile Lys His Gln
695 700 705

CAG CCC TCC GCC GCC GCT GCC ACC ATC GCC GCC AGC GAC AGC TCC CTC 288
Gln Pro Ser Ala Ala Ala Ala Thr Ile Ala Ala Ser Asp Ser Ser Leu
710 715 720

AAG TTC ACC CAT GTC CTC TAC AAC CTC TCC CCC GCT GAG TTG TAC GAG 336
Lys Phe Thr His Val Leu Tyr Asn Leu Ser Pro Ala Glu Leu Tyr Glu
725 730 735

CAG GCT TTC GGC CAA AAG AAG AGT TCG TTC ATC ACG TCG ACC GGC GCG 384
Gln Ala Phe Gly Gln Lys Lys Ser Ser Phe Ile Thr Ser Thr Gly Ala
740 745 750

CTG GCC ACG CTG TCC GGC GCC AAG ACC GGC CGG TCG CCC AGG GAC AAG 432
Leu Ala Thr Leu Ser Gly Ala Lys Thr Gly Arg Ser Pro Arg Asp Lys
755 760 765 770

CGT GTC GTC AAG GAC GAG ACC ACC TCA CAG GAG CTC TGG TGG GGC AAG 480
Arg Val Val Lys Asp Glu Thr Thr Ser Gln Glu Leu Trp Trp Gly Lys
775 780 785

GGC TCG CCC AAC ATC GAG ATG GAC GAG CGC CAG TTC GTG ATC AAC AGG 528
Gly Ser Pro Asn Ile Glu Met Asp Glu Arg Gln Phe Val Ile Asn Arg
790 795 800

GAG CGG GCC CTG GAC TAC CTC AAC TCA CTG GAC AAG GTG TAC GTC AAC 576
Glu Arg Ala Leu Asp Tyr Leu Asn Ser Leu Asp Lys Val Tyr Val Asn
805 810 815

GAC CAG TTC CTC AAC TGG GAC TCG GAG AAC CGC ATC AAG GTC CGC ATC 624
Asp Gln Phe Leu Asn Trp Asp Ser Glu Asn Arg Ile Lys Val Arg Ile
820 825 830

ATC ACC TCC AGG GCG TAC CAC GCC CTC TTT ATG CAC AAC ATG TGC ATC 672
Ile Thr Ser Arg Ala Tyr His Ala Leu Phe Met His Asn Met Cys Ile
835 840 845 850

CGG CCC ACG GAA GAG GAG CTG GAG AGC TTC GGC ACG CCG GAC TTC ACC 720
Arg Pro Thr Glu Glu Glu Leu Glu Ser Phe Gly Thr Pro Asp Phe Thr
855 860 865

ATT TAC AAC GCC GGG GAG TTC CCC GCC AAC CGT TAC GCC AAC TAC ATG 768

-continued

```
Ile Tyr Asn Ala Gly Glu Phe Pro Ala Asn Arg Tyr Ala Asn Tyr Met
            870                 875                 880

ACG TCG TCG ACG AGC ATA AAC ATC AGC CTC GCT AGG AGG GAG ATG GTA       816
Thr Ser Ser Thr Ser Ile Asn Ile Ser Leu Ala Arg Arg Glu Met Val
        885                 890                 895

ATC CTG GGC ACG CAG TAC GCC GGG GAG ATG AAG AAG GGG CTC TTT GGC       864
Ile Leu Gly Thr Gln Tyr Ala Gly Glu Met Lys Lys Gly Leu Phe Gly
    900                 905                 910

GTC ATG CAC TAC CTC ATG CCC AAG CGA GGC ATC CTC TCG CTG CAC TCC       912
Val Met His Tyr Leu Met Pro Lys Arg Gly Ile Leu Ser Leu His Ser
915                 920                 925                 930

GGG TGC AAC ATG GGC AAG GAG GGT GAC GTC GCC CTC TTC TTT GGG CTC       960
Gly Cys Asn Met Gly Lys Glu Gly Asp Val Ala Leu Phe Phe Gly Leu
                935                 940                 945

TCA GGT ACC GGG AAG ACG ACG CTG TCA ACT GAC CAC AAC AGG CTC CTG      1008
Ser Gly Thr Gly Lys Thr Thr Leu Ser Thr Asp His Asn Arg Leu Leu
            950                 955                 960

ATC GGT GAT GAC GAG CAC TGC TGG AGC GAC AAT GGC GTC TCC AAC ATT      1056
Ile Gly Asp Asp Glu His Cys Trp Ser Asp Asn Gly Val Ser Asn Ile
        965                 970                 975

GAG GGA GGT TGC TAT GCC AAG TGC ATC GAC CTG TCC AAG GAG AAA GAA      1104
Glu Gly Gly Cys Tyr Ala Lys Cys Ile Asp Leu Ser Lys Glu Lys Glu
    980                 985                 990

CCT GAT ATC TGG AAC GCC ATC ACG TTT GGA ACA GTG CTG GAA AAC GTC      1152
Pro Asp Ile Trp Asn Ala Ile Thr Phe Gly Thr Val Leu Glu Asn Val
995                 1000                1005                1010

GTC TTC AAC GAG CGC ACT CGT GAA GTT GAC TAC GCC GAC AAA TCT ATC      1200
Val Phe Asn Glu Arg Thr Arg Glu Val Asp Tyr Ala Asp Lys Ser Ile
                1015                1020                1025

ACC GAG AAC ACC CGG GCC GCC TAC CCG ATC GAG TTC ATC CCC AAC GCC      1248
Thr Glu Asn Thr Arg Ala Ala Tyr Pro Ile Glu Phe Ile Pro Asn Ala
            1030                1035                1040

AAG ATC CCA TGC GTC GGG CCG CAC CCC AAG AAC GTC ATC CTC CTG GCC      1296
Lys Ile Pro Cys Val Gly Pro His Pro Lys Asn Val Ile Leu Leu Ala
        1045                1050                1055

TGC GAC GCG TAC GGC GTG CTC CCG CCG GTG AGC AAG CTC AAC CTG GCG      1344
Cys Asp Ala Tyr Gly Val Leu Pro Pro Val Ser Lys Leu Asn Leu Ala
    1060                1065                1070

CAG ACC ATG TAC CAC TTC ATC AGC GGC TAC ACT GCC ATC GTC GCC GGC      1392
Gln Thr Met Tyr His Phe Ile Ser Gly Tyr Thr Ala Ile Val Ala Gly
1075                1080                1085                1090

ACG GAG GAC GGC GTC AAG GAG CCG ACG GCG ACC TTC TCG GCC TGC TTC      1440
Thr Glu Asp Gly Val Lys Glu Pro Thr Ala Thr Phe Ser Ala Cys Phe
                1095                1100                1105

GGC GCG GCC TTC ATC ATG TAC CAC CCC ACC AAG TAC GCC GCC ATG CTC      1488
Gly Ala Ala Phe Ile Met Tyr His Pro Thr Lys Tyr Ala Ala Met Leu
            1110                1115                1120

GCC GAG AAG ATG CAG AAG TAC GGC CGC ACC GGG TGG CTT GTC AAC ACC      1536
Ala Glu Lys Met Gln Lys Tyr Gly Arg Thr Gly Trp Leu Val Asn Thr
        1125                1130                1135

GGC TGG TCC GGC GGC AGG TAC GGT GTG GGC AAC AGG ATC AAG CTG CCG      1584
Gly Trp Ser Gly Gly Arg Tyr Gly Val Gly Asn Arg Ile Lys Leu Pro
    1140                1145                1150

TAC ACC AGG AAG ATC ATC GAC GCC ATC CAC TCC GGC GAG CTC CTC ACC      1632
Tyr Thr Arg Lys Ile Ile Asp Ala Ile His Ser Gly Glu Leu Leu Thr
1155                1160                1165                1170

GCC AAC TAC AAG AAG ACC GAG GTG TTC GGG CTG GAG ATC CCC ACC GAG      1680
Ala Asn Tyr Lys Lys Thr Glu Val Phe Gly Leu Glu Ile Pro Thr Glu
                1175                1180                1185

ATC AAC GGC GTG CCG TCG GAA ATC CTC GAC CCC GTC AAC ACC TGG ACG      1728
```

-continued

```
Ile Asn Gly Val Pro Ser Glu Ile Leu Asp Pro Val Asn Thr Trp Thr
            1190                1195                1200

GAC AAG GCC GCG TAC AAG GAG ACT CTC CTG AAG CTT GCC GGG CTC TTC    1776
Asp Lys Ala Ala Tyr Lys Glu Thr Leu Leu Lys Leu Ala Gly Leu Phe
        1205                1210                1215

AAG AAC AAC TTC GAG GTG TTC GCC AGC TAC AAG ATC GGG GAC GAC AAC    1824
Lys Asn Asn Phe Glu Val Phe Ala Ser Tyr Lys Ile Gly Asp Asp Asn
    1220                1225                1230

AGC CTG ACC GAA CAG ATC CTT GCC GCA GGC CCC AAC TTC TGATTCCAAG     1873
Ser Leu Thr Glu Gln Ile Leu Ala Ala Gly Pro Asn Phe
1235                1240                1245

CAATGGATCC GGAACGGCGA GGCGTTGGAG TTGGTTCAGA ATGAACCAGT GGTGCGTGTG  1933

TGCGTGCGTG TGTTACGATG ATGATGATGA TGGCGAAAAA AAAACTGTTG GACTGATGAT  1993

GTGCCAACAT GGAGTAGACC AGCTCTGTAT GCTATCATGT GTGTGTGGTG TTGTTACCTG  2053

TGGTTTGTTC TATCTGGGCG TGGTCCTGGT GTAAATCTGT ATGCCTGTTC GGCGGC      2109
```

( 2 ) INFORMATION FOR SEQ ID NO:6:

( i ) SEQUENCE CHARACTERISTICS:
( A ) LENGTH: 621 amino acids
( B ) TYPE: amino acid
( D ) TOPOLOGY: linear ( i i ) MOLECULE TYPE: protein ( x i ) SEQUENCE DESCRIPTION: SEQ ID NO:6:

```
Met Ala Pro Ser Val Met Ala Ser Ser Ala Thr Thr Val Ala Pro Phe
  1               5                  10                  15

Gln Gly Leu Lys Ser Thr Ala Gly Met Pro Val Ala Arg Arg Ser Gly
             20                  25                  30

Asn Ser Ser Phe Gly Asn Val Ser Asn Gly Gly Arg Ile Arg Cys Met
         35                  40                  45

Gln Ser Arg Ser Leu Ala Arg Glu Tyr Gly Pro Asn Leu Val Lys Gly
     50                  55                  60

Asp Pro Glu Ala Thr Lys Gly Ala Pro Pro Val Pro Ile Lys His Gln
 65                  70                  75                  80

Gln Pro Ser Ala Ala Ala Ala Thr Ile Ala Ala Ser Asp Ser Ser Leu
                 85                  90                  95

Lys Phe Thr His Val Leu Tyr Asn Leu Ser Pro Ala Glu Leu Tyr Glu
            100                 105                 110

Gln Ala Phe Gly Gln Lys Lys Ser Ser Phe Ile Thr Ser Thr Gly Ala
        115                 120                 125

Leu Ala Thr Leu Ser Gly Ala Lys Thr Gly Arg Ser Pro Arg Asp Lys
    130                 135                 140

Arg Val Val Lys Asp Glu Thr Thr Ser Gln Glu Leu Trp Trp Gly Lys
145                 150                 155                 160

Gly Ser Pro Asn Ile Glu Met Asp Glu Arg Gln Phe Val Ile Asn Arg
                165                 170                 175

Glu Arg Ala Leu Asp Tyr Leu Asn Ser Leu Asp Lys Val Tyr Val Asn
            180                 185                 190

Asp Gln Phe Leu Asn Trp Asp Ser Glu Asn Arg Ile Lys Val Arg Ile
        195                 200                 205

Ile Thr Ser Arg Ala Tyr His Ala Leu Phe Met His Asn Met Cys Ile
    210                 215                 220

Arg Pro Thr Glu Glu Glu Leu Glu Ser Phe Gly Thr Pro Asp Phe Thr
225                 230                 235                 240
```

-continued

Ile Tyr Asn Ala Gly Glu Phe Pro Ala Asn Arg Tyr Ala Asn Tyr Met
245 250 255

Thr Ser Ser Thr Ser Ile Asn Ile Ser Leu Ala Arg Arg Glu Met Val
260 265 270

Ile Leu Gly Thr Gln Tyr Ala Gly Glu Met Lys Lys Gly Leu Phe Gly
275 280 285

Val Met His Tyr Leu Met Pro Lys Arg Gly Ile Leu Ser Leu His Ser
290 295 300

Gly Cys Asn Met Gly Lys Glu Gly Asp Val Ala Leu Phe Phe Gly Leu
305 310 315 320

Ser Gly Thr Gly Lys Thr Thr Leu Ser Thr Asp His Asn Arg Leu Leu
325 330 335

Ile Gly Asp Asp Glu His Cys Trp Ser Asp Asn Gly Val Ser Asn Ile
340 345 350

Glu Gly Gly Cys Tyr Ala Lys Cys Ile Asp Leu Ser Lys Glu Lys Glu
355 360 365

Pro Asp Ile Trp Asn Ala Ile Thr Phe Gly Thr Val Leu Glu Asn Val
370 375 380

Val Phe Asn Glu Arg Thr Arg Glu Val Asp Tyr Ala Asp Lys Ser Ile
385 390 395 400

Thr Glu Asn Thr Arg Ala Ala Tyr Pro Ile Glu Phe Ile Pro Asn Ala
405 410 415

Lys Ile Pro Cys Val Gly Pro His Pro Lys Asn Val Ile Leu Leu Ala
420 425 430

Cys Asp Ala Tyr Gly Val Leu Pro Pro Val Ser Lys Leu Asn Leu Ala
435 440 445

Gln Thr Met Tyr His Phe Ile Ser Gly Tyr Thr Ala Ile Val Ala Gly
450 455 460

Thr Glu Asp Gly Val Lys Glu Pro Thr Ala Thr Phe Ser Ala Cys Phe
465 470 475 480

Gly Ala Ala Phe Ile Met Tyr His Pro Thr Lys Tyr Ala Ala Met Leu
485 490 495

Ala Glu Lys Met Gln Lys Tyr Gly Arg Thr Gly Trp Leu Val Asn Thr
500 505 510

Gly Trp Ser Gly Gly Arg Tyr Gly Val Gly Asn Arg Ile Lys Leu Pro
515 520 525

Tyr Thr Arg Lys Ile Ile Asp Ala Ile His Ser Gly Glu Leu Leu Thr
530 535 540

Ala Asn Tyr Lys Lys Thr Glu Val Phe Gly Leu Glu Ile Pro Thr Glu
545 550 555 560

Ile Asn Gly Val Pro Ser Glu Ile Leu Asp Pro Val Asn Thr Trp Thr
565 570 575

Asp Lys Ala Ala Tyr Lys Glu Thr Leu Leu Lys Leu Ala Gly Leu Phe
580 585 590

Lys Asn Asn Phe Glu Val Phe Ala Ser Tyr Lys Ile Gly Asp Asp Asn
595 600 605

Ser Leu Thr Glu Gln Ile Leu Ala Ala Gly Pro Asn Phe
610 615 620

( 2 ) INFORMATION FOR SEQ ID NO:7:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "forward primer"

( x i ) SEQUENCE DESCRIPTION: SEQ ID NO:7:

AGACGACTCT TAGCCACAGC C 21

( 2 ) INFORMATION FOR SEQ ID NO:8:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "reverse primer"

( x i ) SEQUENCE DESCRIPTION: SEQ ID NO:8:

TCGATGGAGT GGTGCTTCTC 20

( 2 ) INFORMATION FOR SEQ ID NO:9:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "forward primer"

( x i ) SEQUENCE DESCRIPTION: SEQ ID NO:9:

GGAATTCCAT GGTGCATCTC AAGAAGTAC 29

( 2 ) INFORMATION FOR SEQ ID NO:10:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "reverse primer"

( x i ) SEQUENCE DESCRIPTION: SEQ ID NO:10:

GCTCTAGACT GCATGCACCT GATCC 25

DNA ENCODING PHOSPHOENOLPYRUVATE CARBOXYKINASE, RECOMBINANT VECTOR AND TRANSFORMED PLANT CONTAINING THE SAME

This application is a 371 of PCT/JP95/01356 filed Jul. 6, 1995.

TECHNICAL FIELD

The present invention relates to a phosphoenolpyruvate carboxykinase (hereinafter also referred to as "PCK") gene and to a recombinant vector containing the same.

BACKGROUND ART

PCK is an enzyme which reversibly catalyzes the reaction forming oxaloacetic acid by carboxylation of phosphoenolpyruvate. ATP-dependent PCK (EC 4.1.1.49) and GTP-dependent PCK (EC 4.1.1.32) are known. Plant PCKs are dependent on ATP and play an important role in the process of photosynthesis by which starch is formed from carbon dioxide.

On the other hand, $C_4$ plants include mainly the plants belonging to family Gramineae originated in tropical zone, and are well adapted for strong sun light, high temperature and to shortage of water. More particularly, the rate of photosynthesis of $C_4$ plants is twice that of $C_3$ plants, and the photosynthesis is not inhibited by oxygen in the air. The photosynthesis of $C_4$ plants does not reach saturation even if they are irradiated with a light having an intensity by which the photosynthesis of $C_3$ plants is saturated. Further, the optimum temperature for photosynthesis of $C_4$ plants is higher than that of $C_3$ plants.

As mentioned above, PCK of plants plays an important role in photosynthesis. Thus, if a $C_3$ plant is transformed so that it produces the PCK of $C_4$ plant, it is expected that various effects may be obtained, such as increase in the rate of photosynthesis, efficient utilization of the sun light, and promotion of photosynthesis at a high temperature. However, so far, PCK gene of plants, needless to say $C_4$ plants, has not been entirely sequenced.

DISCLOSURE OF THE INVENTION

Accordingly, an object of the present invention is to provide a cloned PCK gene of a $C_4$ plant, a recombinant vector containing the gene, and a plant transformed with the recombinant vector.

The present inventors succeeded in cloning the PCK gene of *Urochloa panicoides* which is a $C_4$ plant and in determining the entire sequence of the gene as well as deduced amino acid sequence encoded by the gene. The present inventors further succeeded in constructing a recombinant vector containing the PCK gene and in transforming a plant with the recombinant vector to obtain a transformed plant which expresses the PCK gene, thereby completing the present invention.

That is, the present invention provides a cloned DNA encoding the amino acid sequence shown in SEQ ID NOS: 1–6 in Sequence Listing or the same amino acid sequence as shown in SEQ ID NOS: 1–6 except that one or more amino acid is added, deleted, inserted or substituted, with the proviso that the polypeptide having this amino acid sequence has phosphoenolpyruvate carboxykinase activity. The present invention also provides a recombinant vector comprising the DNA according to the present invention, which can express said DNA in a host cell. The present invention further provides a plant transformed with the recombinant vector according to the present invention, which produces phosphoenolpyruvate carboxykinase.

By the present invention, the PCK gene of *Urochloa panicoides* was cloned and its nucleotide sequence was determined. It is expected that by introducing this gene into a $C_3$ plant, the efficiency of photosynthesis may be promoted, photo energy may be more efficiently utilized and resistance to high temperature of the plant may also be promoted.

BRIEF DESCRIPTION OF THE DRAWINGS

FIG. 3 shows the amino acid sequence encoded by PCK1 in comparison with that encoded by PCK2;

BEST MODE FOR CARRYING OUT THE INVENTION

Figure 1:
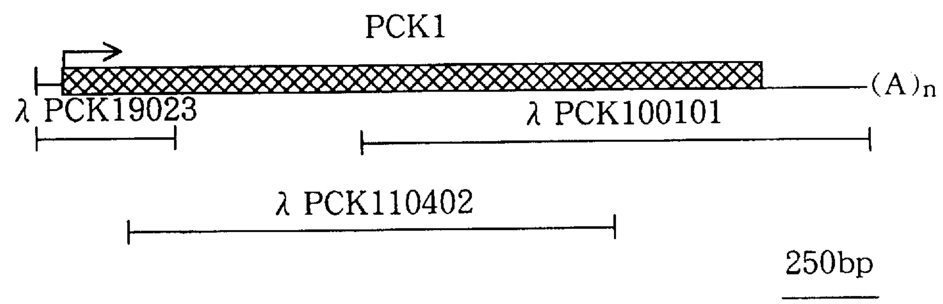
FIG. 1 shows the positions and lengths of the cDNAs employed for obtaining PCK1 which is a full length cDNA sequence of *Urochloa panicoides;*

The gene according to the present invention was cloned by preparing a cDNA library from green leaves of *Urochloa panicoides* by a conventional method, and identifying a PCK-producing clone by immunoblotting method employing an anti-PCK antibody. The nucleotide sequence of the gene was determined by sequencing the cDNA insert in the clone and the amino acid sequence encoded thereby was deduced. The molecular weight of the protein having the deduced amino acid sequence is identical to that of purified PCK, so that the gene is thought to encode full length of PCK. The above-mentioned method is detailed in the examples hereinbelow described.

By the above-mentioned method, the nucleotide sequences shown in SEQ ID NOS: 1 and 3 in Sequence Listing were determined. The present invention provides cloned DNAs encoding the amino acid sequences shown in SEQ ID NOS: 1–4, respectively. Further, as will be described concretely in the examples described below, the N-terminal of active PCK of *Urochloa panicoides* was determined. As a result, active PCKs whose N-terminals are serine which is the 57th amino acid, glutamic acid which is the 61st amino acid, leucine which is the 66th amino acid, glycine which is the 69th amino acid and glycine which is the 75th amino acid, respectively, of the amino acid sequence shown in SEQ ID NO: 2, were detected. Thus, it is seen from this fact that amino acid sequence from the 75th amino acid glycine to the C-terminal is sufficient for exerting PCK activity. From the fact that an active PCK which has a N-terminal upstream of the 57th amino acid serine of SEQ ID NO. 1 was not found, it is assumed that the amino acid sequence from the 1st amino acid methionine to the 56th amino acid alanine is cut off during the purification process of PCK protein. This was confirmed in the examples described below by expressing a DNA comprising a sequence in the small subunit of Rubisco of rice prepared from rice genome DNA and the DNA encoding the polypeptide region from the 57th amino acid serine to the C-terminal.

Further, in the examples below, the amino acid sequences shown in SEQ ID NOS:1–4 were ligated at the KpnI site (a part of the amino acid sequence shown in SEQ ID NO: 3 is in the upstream side), and a DNA encoding an amino acid sequence of the transit peptide originated from the small subunit of Rubisco of rice was ligated to the upstream of the above-mentioned ligated DNA (SEQ ID NO: 5). The amino acid sequence from the 52nd serine to the C-terminal encodes the mature PCK protein. It was confirmed that the rice plant transformed with this DNA produced PCK encoded by this DNA, which PCK had a PCK activity. Thus, DNAs prepared by ligating parts of a plurality of naturally occurring PCK genes are also within the scope of the present invention.

It is well-known in the art that there are cases wherein the physiological activity of a physiologically active peptide is retained even if the amino acid sequence of the peptide is modified to a small extent, that is, even if one or more amino acids in the amino acid sequence are substituted or deleted, or even if one or more amino acids are added or inserted to the amino acid sequence. The DNA fragments which encode polypeptides having such modifications, that have PCK activity are included within the scope of the present invention. Therefore, DNAs encoding the polypeptide having the same amino acid sequence as shown in SEQ ID NOS: 1–6, except that one or more amino acid are added, inserted, deleted or substituted, which has PCK activity, are also within the scope of the present invention.

Modification of DNA which brings about addition, insertion, deletion or substitution of the amino acid sequence encoded thereby can be attained by the site-specific mutagenesis which is well-known in the art (e.g., Nucleic Acid Research, Vol. 10, No. 20, p6487–6500, 1982). In the present specification, "one or more amino acids" means the number of amino acids which can be added, inserted, deleted or substituted by the site-specific mutagenesis.

Site-specific mutagenesis may be carried out by, for example, using a synthetic oligonucleotide primer complementary to a single-stranded phage DNA except that the desired mutation as follows. That is, using the above-mentioned synthetic oligonucleotide as a primer, a complementary chain is produced by a phage, and host bacterial cells are transformed with the obtained double-stranded DNA. The culture of the transformed bacterial cells is plated on agar and plaques are formed from a single cell containing the phage. Theoretically, 50% of the new colonies contain the phage having a single-stranded chain carrying the mutation and remaining 50% of the colonies contain the phage having the original sequence. The obtained plaques are then subjected to hybridization with a kinase-treated synthetic probe at a temperature at which the probe is hybridized with the DNA having exactly the same sequence as the DNA having the desired mutation but not with the original DNA sequence that is not completely complementary with the probe. Then the plaques in which the hybridization was observed are picked up, cultured and the DNA is collected.

In addition to the above-mentioned site-specific mutagenesis, the methods for substituting, deleting, inserting or adding one or more amino acids without losing the enzyme activity include a method in which the gene is treated with a mutagen and a method in which the gene is selectively cleaved, a selected nucleotide is removed, added or substituted and then the gene is ligated.

The DNA according to the present invention may be obtained by the method described in detail in the examples below. Alternatively, since the nucleotide sequence of the PCK gene of *Urochloa panicoides* was determined by the present invention as shown in SEQ ID NOS: 1–6, the gene of the present invention may be obtained easily by PCR method utilizing the genome DNA of *Urochloa panicoides* as a template or by RT-PCR method utilizing cDNAs of *Urochloa panicoides* as a template.

The DNA according to the present invention may be inserted into an expression vector for plants to obtain a recombinant vector. A transformed plant which can express the PCK of *Urochloa panicoides* may be obtained by transforming a plant with the obtained recombinant vector. The method for transforming plants has already been established, and the method employing *Agrobacterium tumefaciens* is preferably employed. The transformation method employing *Agrobacterium tumefaciens* is well-known in the art and dicotyledons (e.g., Japanese. Laid-open Patent Application (Kokai) No. 4-330234) as well as monocotyledons (WO 94/00977) may be transformed. Suitable plants for introducing the PCK gene according to the present invention include rice, maize, tomato, tobacco and the like, although the plants are not restricted thereto. An example of the method for transformation is described in detail in the examples described below.

EXAMPLES

The present invention will now be described more concretely by way of examples. It should be noted, however, the present invention is not restricted to the following examples.

Example 1

Cloning and Identification of PCK1

(I) Materials and Method (1) Plant Material

All plant material used for RNA isolations was from *U. panicoides* accession CQ2798, supplied by CSIRO, Division of Tropical Crops and Pastures, Brisbane, Queensland, Australia. Light grown plants were grown in full sunlight for 5 weeks during the summer months. Dark grown plants were grown at 28° C. from seeds sown on wet tissue in aluminum foil-wrapped polystyrene boxes.

(2) Purification of PCK

PCK was purified from light grown *U. panicoides* leaves essentially as described in Burnell JN, Purification and properties of phosphoenolpyruvate carboxykinase from $C_4$ plants. Aust. J. Plant Physiol. 13:577–587 (1986), except that a second DEAE-Sepharose CL-6B column (commercially available from Pharmacia) was omitted. Between 100 $\mu$g and 200 $\mu$g protein in 1 ml from the Sephacryl S-300 column (commercially available from Pharmacia) fractions containing peak PCK activity was combined with an equal volume of 125 mM Tris HCl, pH 6.8, 20% glycerol, 4% SDS, 10% 2-mercaptoethanol, 0.0025% Bromphenol blue and heated at 85° C. for 2 minutes. Samples were clarified at 12,000×g for 5 minutes before separation on 16 cm×18 cm×0.2 cm 10% SDS-polyacrylamide resolving gels according to a known method (Laemmli UK: Cleavage of structural proteins during the assembly of the head of bacteriophage T4, Nature 227: 680–685 (1970)). Gels were stained for 1 hour in 0.5% Coomassie blue R-250, 40% ethanol, 10% acetic acid and destained with 10% methanol,. 10% acetic acid.

In preparation for electroelution, stained protein bands were excised, equilibrated with 0.15 M NaCl, 1% SDS, 50 mM Tris HCl, pH 7.5 and then with 10 mM Tris acetate, pH 8.6, 1 mM EDTA, 1% SDS. Gel slices were broken up by passing through a 5 ml syringe barrel and placed into the anode well of the trap from a Little Blue Tank (trademark) electroelution apparatus (ISCO, USA). The trap was filled with 10 mM Tris acetate, pH 8.6, 1 mM EDTA, 1% SDS while the anode and cathode chambers were filled with 40 mM Tris acetate, pH 8.6, 1 mM EDTA, 1% SDS. Electroelution was carried out at 3 W constant power for 3 hours. The recovery of protein from the cathode well of the trap was >90%. The electroeluted PCK was concentrated by centrifugation in Centricon-30 (trademark) ultrafiltration capsules (Amicon, Australia), diluted 100-fold with PBS (15 mM sodium phosphate, pH 7.2, 140 mM NaCl, 3 mM KCl) and reconcentrated.

(3) Preparation of Anti-PCK Antiserum

Approximately 500 μg of gel purified PCK in 500 μl PBS was mixed with an equal volume of Freund's complete adjuvant. Aliquots (500 μl) of the mixture were injected intramuscularly into each thigh of a rabbit (New Zealand long-earred variety). The rabbit was boosted as above, except Freund's incomplete adjuvant was used, 30 days and 48 days after the initial injection. Blood was collected from an ear vein at the time of the second boost and then 10 to 14 days intervals. Blood samples were allowed to clot before clarifying by centrifugation at 1000×g for 10 minutes. Clarified serum was made 0.02% in sodium azide and stored at 4° C.

(4) Electroblotting and Immunodetection of PCK

Proteins were separated by SDS-PAGE on 10% acrylamide resolving gels (Laemmli, supra) and either stained with Coomassie blue R-250 or used for electroblotting. For immunoblotting experiments, gels were equilibrated in 25 mM Tris, 192 mM glycine, 20% methanol prior to electroblotting to nitrocellulose membrane (Schleicher and Schuell, Germany) with this buffer in a Trans-Blot (trademark) chamber (Bio-Rad, Australia) on ice for 1 hour at 250 mA. Blots were blocked with 0.5% skim milk powder in TBST (12.5 mM Tris HCl, pH 8.0, 137 mM NaCl, 2.7 mM KCl, 0.1% Tween 20) for 16 hours before adding clarified rabbit anti-PCK antiserum and incubating for 1 hour. Blots were washed 3 times for 10 minutes with TBST and the bound antibody detected using the ProtBlot (trademark) detection system according to the manufacturer's specifications (Promega, Australia). For N-terminal amino acid sequence determination, proteins were transferred to polyvinylidene difluoride (PVDF) membrane (Bio-Rad, Australia) by electroblotting as above except the tank buffer used was 10 nM CAPS, pH 11, 10% methanol. Blots were stained with 0.1% Coomassie blue R-250 in 50% methanol, destained with 50% methanol and air dried. The protein bands to be used in the sequence determination were excised.

(5) Isolation of RNA from *U. panicoides*

Total RNA was purified from various *U. panicoides* tissues after the method of Chomczynski and Sacchi (Chomczynski P, Sacchi N: Single-step method of RNA isolation by acid guanidinium thiocyanate phenol chloroform extraction. Anal. Biochem. 162: 156–159 (1987)). Poly(A)$^+$RNA was isolated from total RNA by batch treatment with oligo-(dT)$_{25}$-conjugated paramagnetic particles (Dynal, Norway) according to the manufacturer's procedure.

(6) Construction and Screening of *U. panicoides* cDNA Library

A directional cDNA library was constructed in λgt11D from 3 μg *U. panicoides* poly(A)$^+$RNA using a TimeSaver (trademark) cDNA synthesis kit (Amrad-Pharmacia, Australia) according to the supplier's instructions. The library was packaged using Gigapack II (trademark) packaging extracts (Stratagene, USA), and titred and amplified on Y1088 plating bacteria (Sambrook J, Fritsch EF, Maniatis T: Molecular Cloning. A Laboratory Manual, 2nd ed. Cold Spring harbor laboratory Press, Cold Spring Harbor N.Y. (1989)). Transfers were blocked for 1 hour as above for immunoblots before incubating for 16 hours in 50 ml TBST containing 10 μl rabbit anti-PCK antiserum.

Transfers were washed and bound antibody detected as in immunoblotting experiments.

For screening by hybridization, plaques were transferred to Hybond-N$^+$ (trademark)(Amersham, Australia), denatured and phage DNA fixed with 0.4 M NaOH as recommended by the manufacturer. Membranes were prehybridized 1 hour at 42° C. in 5×SSC (1×=0.15 M NaCl, 15 mM trisodium citrate), 50% formamide, 0.1% SDS, 50 mM sodium phosphate (pH 7.0), 0.1% Ficoll (trademark) (Amrad-Pharmacia, Australia), 0.1% polyvinylpyrrolidone, 0.1% bovine serum albumin, 250 μg/ml heat-denatured herring sperm DNA before adding a heat denatured radiolabeled probe. DNA restriction fragment probes were purified from agarose gels (Sambrook J., et al., supra) and radiolabeled with [$\alpha$-$^{32}$P] dCTP (NEN-DuPont, Australia) by random priming using a GIGAprime DNA labeling kit (Bresatec, Australia). Hybridization was conducted at 42° C. for 16 hours before membranes were washed twice in 2×SSC, 0.1% SDS at 42° C. for 15 minutes and twice in 0.1×SSC, 0.1% SDS at 65° C. for 15 minutes.

(7) Subclonin and Sequencing cDNA inserts

Phage DNA was prepared from plate lysates and the inserts were subcloned into pBluescript II-KS (trademark, Stratagene, USA) using standard procedure (Sambrook J. et al., supra). For sequencing, sets of nested deletions were constructed using exonuclease III (Henikoff S: Unidirectional digestion with exonuclease III creates targeted breakpoints for DNA sequencing. Gene 28: 351–359 (1984)) followed by mung bean nuclease digestion before re-ligation. Alkaline lysis mini preparations (Sambrook J. et al., supra) of appropriate deletion plasmids were denatured by boiling in alkali (Yie Y. Wei Z, Tien P: A simplified and reliable protocol for plasmid DNA sequencing: fast miniprep and denaturation. Nucleic Acids Res 21:361 (1993)) and sequenced using the dideoxy chain termination method (Sanger F, Nicklen S, Coulson AR: DNA sequencing with chain terminating inhibitors. Proc. Natl. Acad. Sci. USA 74: 5463–5467 (1977)) with a T7 sequencing kit (trademark, Amrad-Pharmacia, Australia). Restriction enzymes and other nucleic acid modifying enzymes were from Amrad-Pharmacia, Australia.

(8) Northern Analysis

Poly(A)$^+$RNA was separated on a 1.2% agarose gel containing 8 mM formaldehyde (Sambrook J. et al., supra). The RNA was transferred to Hybond-N$^+$(trademark) for 2 hours under 75 mm Hg pressure using 0.4 M NaOH as the buffer. Membranes were pre-hybridized at 42° C. for 3–4 hours in 0.9 M NaCl, 6 mM EDTA, 60 mM $NaH_2PO_4$, pH 7.4, 50% formamide, 0.1% SDS, 10% dextran sulphate, 0.04% Ficoll (trademark), 0.04% polyvinylpyrrolidone, 0.04% bovine serum albumin, 0.5 mg/ml denatured herring sperm DNA. Heat denatured radiolabeled restriction fragments were added and hybridization was conducted at 42° C. for 16 hours. Membranes were washed as described above for plaque lifts.

Results (1) Preparation of Rabbit Anti-*U. panicoides* PCK Antiserum

The first step in the molecular characterization of *U. panicoides* PCK was to obtain an antiserum against purified PCK. Ammonium sulphate fractionation followed by ion exchange and molecular sieve column chromatography was used to purify PCK from field grown *U. panicoides* according to Burnell JN (supra). Protein from the peak fraction obtained from Sephacryl S-300 (Pharmacia) column chromatography was separated by SDS-PAGE. Staining with Coomassie blue revealed five protein species of approximately 69, 63, 62, 61 and 60 kDa. The most abundant species, migrating at 62 kDa, was presumed to be PCK and was gel purified. The final purified product appeared to be homogenous upon SDS-PAGE and, so, was used as the antigen for the production of a rabbit antiserum.

The resulting antiserum was used to probe an immunoblot of the same column faction used for the antigen purification. The pattern obtained was identical to the Coomassie stained profile in both the proteins detected and the relative staining intensities of the five species. However, when a crude tissue extract of *U. panicoides* was probed with this antiserum, subtle differences in staining intensity were seen. In the crude extract, the 63, 62 and 61 kDa species stained with equal intensity while the 60 kDa species stained a great deal less intensely while in the purified PCK, the 63 kDa species stained less intensely than the other species.

(2) Cloning and Sequence Analysis of PCK cDNA

Poly(A)$^+$ RNA isolated from green leaves of field grown *U. panicoides* was used to construct a cDNA expression library in a λgt11 derivative vector. When $2\times10^5$ plaques of this library were screened with the anti-PCK antiserum, 40 immunoreactive clones were obtained. Twelve of these were re-screened to homogeneity. The cDNA inserts were subcloned and the ends sequenced. All 12 inserts had homology to the PCK sequence of *Saccharomyces cerevisiae* (Stucka R et al., Nucleotide sequence of the phosphoenolpyruvate carboxykinase gene from *Saccaromyces cerevisiae*. Nucleic Acids Res 16: 10926 (1988)). The longest insert, that of λPCK100101, was 1.4 kb and thus was insufficient to encode the approximately 62 kDa PCK protein. To obtain cDNAs covering the entire PCK open reading frame, the library was rescreened with radiolabeled restriction fragments from the 5' ends of cDNAs extending progressively more in the 3' direction. The resulting overlapping clones which were completely sequenced in both directions are shown in FIG. 1. The λPCK110402 insert overlaps the λPCK100101 and λPCK190203 inserts by 675 and 132 bp, respectively. The overlapping regions of these clones have identical sequences.

As a result, a total of 2220 bp of cDNA sequence was determined, encompassing an open reading frame (ORF) of 1872 bp, as shown in SEQ ID NO: 1 in Sequence Listing. This ORF codes for a 624 residue protein. The gene encoding this ORF will be designated PCK1. The PCK1 ORF is flanked by a 288 bp 3' untranslated region extending to a poly(A) tail and a 57 bp 5' untranslated region.

(3) Properties of PCK1 Protein

The molecular mass of the deduced 624 residue PCK1 protein is 68,474 Da. The algorithm of Kyte and Doolittle (Kyte J, Doolittle RF: A simple method for displaying the hydropathic character of a protein, J. Mol. Biol. 157: 105–132 (1982)) indicates that PCK1 has an overall hydrophilic nature with no transmembrane domains according to the criteria of Popot and de Vitry (Popot J-L, de Vitry C: On the microassembly of integral membrane proteins. Annu. Rev. Biophys. Biophys. Chem. 19: 369–403 (1990)). This is consistent with its cytosolic localization.

(4) Amino Terminal Sequence Analysis of PCK

The N-terminal amino acid sequence of *U. panicoides* PCK was determined by direct sequencing. The proteins in the Sephacryl S-300 (Pharmacia) column fraction containing the peak PCK activity were separated by SDS-PAGE such that the 60–63 kDa proteins ran as a single broad band. This material was blotted to PVDF membrane and the entire band subjected to twelve cycles of automated Edman degradation. Each cycle resulted in the release of detectable quantities of either four or five amino acids. From this data, a total of five overlapping sequences corresponding to the amino acid sequence (I-V, residues 57–68, 61–72, 66–77, 69–80, and 75–86 of SEQ ID NO: 2, respectively) (residues 57-86of SEQ ID NO: 2) deduced from the *U. panicoides* PCK cDNA were identified. These sequences are shown in Table 1 below.

TABLE 1

| Method | | Amino Acid Sequence |
|---|---|---|
| Direct Determination[a] | I. | Ser X Ala Arg Glu Tyr Gly Pro Asn Leu Val Lys |
| | II. | X Tyr Gly Pro Asn Leu Val Lys Gly Asp X Glu |
| | III. | Leu Val Lys Gly Asp X Glu Ala Lys Gly Ala X |
| | IV. | Gly Asp Pro Glu Ala Lys Gly Ala X X X X |
| | V. | Gly X Pro Pro Ala X Val Lys X X X X |
| Deduced from cDNA | | Ser Thr Ala Arg Glu Tyr Gly Pro Asn Leu Val Lys Gly Asp Pro Glu Ala Lys Gly Ala Pro Pro Ala Pro Val Lys Gly Gln Gln Ala |

[a]X denotes a sequencing cycle in which the amino acid corresponding to the residue predicted by the cDNA was not found.

As shown in Table 1, all five sequences begin within 19 residues of each other, the most N-terminal starting 56 residues from the initiating methionine. Of the N-termini identified, sequences I and III were the most abundant. In a second experiment, PCK was electrophoresed as mentioned above and each band sequenced separately. However, results were obtained only for the 62 and 61 kDa species. The 62 kDa band yielded N-terminal sequences III and IV only, which correspond to proteins with deduced molecular masses of 61.8 and 61.4 kDa, respectively. The 61 kDa band yielded sequence V only which results in a protein with a deduced mass of 60.8 kDa. Together, the N-terminal sequencing experiments suggest that the 69 kDa *U. panicoides* PCK translation product is processed to a mature protein of between 60.8 and 62.7 kDa by the removal of a 56–75 residue leader sequence. Thus, the present invention also provides DNAs encoding these five protein species.

(5) Effect of light on PCK1 Expression

*U. panicoides* seeds were germinated and seedlings grown in the dark for 7 days before exposing to continuous light for 96 hours. The etiolated shoots were generally 5 to 6 cm in length and weighed 15 to 20 mg. The elongated coleoptiles were white with yellow immature leaves visible through the intact tips. After 6 hour exposure to light, the coleoptile tips had ruptured and the leaf blades had begun to visibly green and expand. The leaves continued to green and expand throughout the 96 hour light treatment. In contrast, the remainder of the coleoptile changed very little with the length and weight of the shoots increasing only slightly during the exposure to light.

Shoots were harvested at various times during the 96 hour light treatment. Total RNA was prepared from these shoots, separated on an agarose gel, blotted and probed with the radiolabeled 1.4 kb insert of λPCK100101. Total RNA from root and green leaf tissue from a light grown plant were also included. In total RNA from the green leaf, the major species detected by the partial PCK cDNA probe is 2.7 kb in length. The probe also hybridizes to a heterogeneous smear of RNAs smaller than 2.7 kb. In experiments where poly(A)$^+$ RNA from green leaves is probed with radiolabeled restriction fragments from each end and the middle of the PCK1 cDNA, only the 2.7 kb RNA is detected. Thus, this species is most probably the PCK1 mRNA, while the heterogeneous smear in the total RNA is due to PCK1 transcripts lacking poly(A) tails. The unpolyadenylated RNAs could arise either from degradation of the PCK1 mRNA or premature termination of PCK1 transcription.

The 1.4 kb cDNA probe does not detect the PCK1 MRNA in total RNA from roots or etiolated shoots. However, after 6 hour greening, the PCK1 mRNA is detected in shoots. The abundance of this RNA increases steadily during the next 84 hours but at no time during the light regime is the PCK mRNA as abundant as in the green leaf. Although the 2.7 kb transcript is present after only 6 hour exposure to light, the heterogeneous smear is not detected until after 48 hour exposure to light.

Example 2

Cloning and Identification of PCK2

Figure 2:
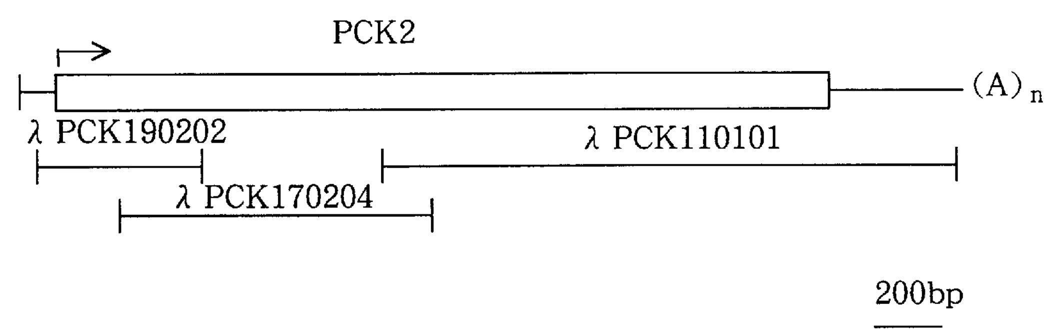
FIG. 2 shows the positions and lengths of the cDNAs employed for obtaining PCK2 which is a full length cDNA sequence of *Urochloa panicoides;*

The same procedure as in Example 1 was repeated. As a result, by analysis of positive clones obtained in isolation of the PCK1 cDNA, a clone having a high homology with PCK1 cDNA but having a nucleotide sequence different from that of PCK1 cDNA was obtained. The overlapping clones are shown in FIG. 2. The λPCK170204 insert overlaps the λPCK190202 and λPCK110101 inserts by 227 and 107 bp, respectively. The overlapping regions of these clones have identical sequences. As a result, a total of 2245 bp of cDNA sequence was determined, encompassing an open reading frame (ORF) of 1878 bp, as shown in SEQ ID NO: 3 in Sequence Listing. This ORF codes for a 626 residue protein. The gene encoding this ORF will be designated PCK2. The PCK2 ORF is flanked by a 304 bp 3' untranslated region extending to a poly(A) tail and a 44 bp 5' untranslated region. The amino acid sequence encoded by PCK3 has a homology of 96% with the amino acid sequence encoded by PCK1, and among the 26 amino acid residues which are not identical, 22 amino acid residues are similar amino acid residues in these amino acid sequences. The comparison between the amino acid sequences of PCK1 and PCK2 is shown in FIG. 3.

Example 3

Introduction of PCK Gene into Rice and Expression

1. Construction of Gene for Expressing PCK cDNA in Plants

Materials and Methods

Plant Material and Isolation of Genome DNA

Genome DNA was extracted from green leaves of a rice plant (*Oryza sativa* cv. Nipponbare) grown in a green house or green leaves of a maize plant (*Zea mays* L. subsp. mays line B73) by the method of Komari et al (Komari T, Saito Y, Nakakido F, Kumashiro T: Efficient selection of somatic hybridsin *Nicotiana tabacum* L. using a combination of drug-resistance markers introduced by transformation. Theor, Appl. Genet. 77:547–552 (1989)).

Manipulation of DNA

Manipulation of DNA was carried out according to standard procedure (Sambrook J. et al., supra). Oligo DNAs were prepared by using a DNA synthesizer 392 (Applied Biosystems, USA). PCR was carried out according to standard procedure (Mcpherson M J, Quirke P, Taylor G R: PCR. A practical approach. Oxford express press, Oxford N.Y. (1991)). For the subcloning of PCR products, TA Cloning kit (trademark, Invitrogen, USA) was used. Sequencing was performed by using DNA cycle sequencing kit (trademark, Applied Biosystems, USA) and Sequencer 373A (Applied Biosystems, USA).

Preparation of Other DNA Regions

A promoter was isolated from maize genome DNA by PCR method using primers synthesized based on the sequence of the promoter region of maize phosphoenolpyruvate carboxylase (Hudspeth R L, Grula J W: Structure and expression of the maize gene encoding the phosphoenolpyruvate carboxylase isozyme involved in C4 photosynthesis. Plant Mol. Biol. 12: 579–589 (1989)). The nucleotide sequences of the used primers were as follows:

Forward primer: 5'-AGACGACTCTTAGCCACAGCC-3' (SEQ ID NO: 7)

Reverse primer: 5'-TCGATGGAGTGGTGCTTCTC-3' (SEQ ID NO: 8)

As the terminator, the cauliflower mosaic virus 35S terminator (SphI-EcoRI fragment) on a plasmid DNA pGL2 (Biland B, Iida S, Peterhans A, Potrykus I, Panszkowski J: The 3'-terminal region of the hygromycin-B- resistance gene is important for its activity in *Escherichia coli* and *Nicotiana tabacum*. Gene 100:247–250 (1991)) was employed.

The region encoding the transit peptide was isolated from rice genome DNA by PCR method using primers synthesized based on the sequence of the rice Rubisco small subunit (Matsuoka M, Kano-Murakami Y, Tanaka Y, Ozeki Y, Yamamoto N: Classification and nucleotide sequence of cDNA encoding the small subunit of ribulose-1,5-bisphosphate carboxylase from rice. Plant Cell Physiol. 29:1015–1022 (1988)). The nucleotide sequences of the used primers were as follows:

Forward primer: 5'-GGAATTCCATGGTGCATCTCAAGAAGTAC-3' (SEQ ID NO: 9)

Reverse primer: 5'-GCTCTAGACTGCATGCACCTGATCC-3' (SEQ ID NO: 10)

The genes encoding PCK to be transported to chloroplasts were ligated at the KpnI site in the inserts of λPCK170204 and λPCK100101, and the above-mentioned gene encoding the transit peptide was ligated at the upstream site of the 57th amino acid serine encoded by PCK2.

In the multicloning site of a plasmid DNA pUC18 (Yanish-Perron C, Vieira J, Messing J: Improved M13 phage cloning vectors and host strains: nucleotide sequences of the M13mp18 and pUC19 vectors. Gene 33:103–119 (1985)), the promoter, the gene encoding the transit peptide and PCK, and the terminator were inserted in the order mentioned. The constructed plasmid was named pPCK.

Figure 4:
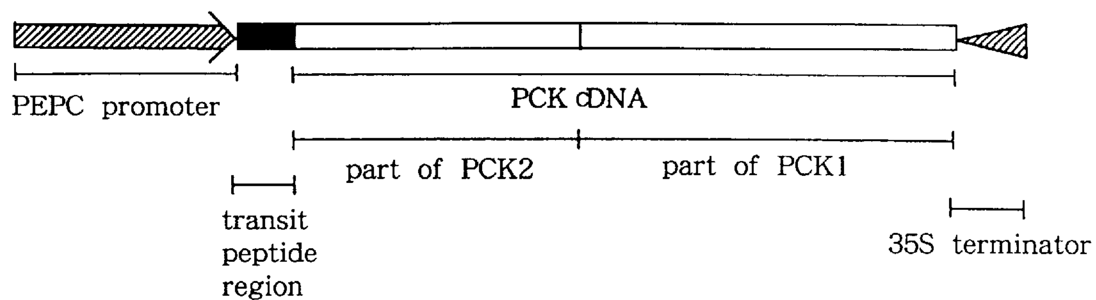
FIG. 4 is a gene map showing inserted DNA region of the recombinant vector used for transformation of rice plants.
Figure 5:
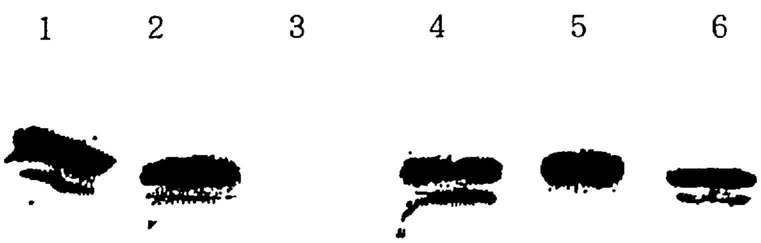
FIG. 5 is a schematic view showing localization of PCK protein in a PCK1+2 chimera-introduced rice transformant. Lane 1 shows the soluble fraction of chloroplasts, Lane 2 shows crude extract of greenleaves+chloroplasts digested with trypsin in ice for 30 minutes, Lane 3 shows disrupted chloroplasts digested with trypsin, Lane 4 shows soluble fraction of chloroplasts treated in ice for 30 minutes, Lane 5 shows crude extract of green leaves and Lane 6 shows chloroplasts digested with trypsin in ice for 30 minutes.

The gene map of the constructed plasmid is shown in FIG. 4. The nucleotide sequence of the constructed cDNA region is shown in SEQ ID NO: 5 in Sequence Listing. In the nucleotide sequence shown in SEQ ID NO: 5, nt1–nt153 is the region encoding the transit peptide originated from rice Rubisco small subunit, nt154–nt966 is the region encoding the N-terminal side of PCK2, and nt967–nt1863 is the region encoding the C-terminal side of PCK1.

2. Transformation of Rice Plants

Materials and Methods

Surfaces of seeds of Japonica rice variety “Tsukinohikari” was sterilized with 70% ethanol for 30 seconds and then with 1% sodium hypochlorite for 40 minutes, and washed three times with sterilized water. The seeds were then placed on 2N6 solid medium and cultured at 30° C. in the dark. The calli dedifferentiated from scutella of immature seeds were subcultured in N6 liquid medium at 25° C. in the dark with a revolution of 125 rpm. The cultured cells were subcultured every week in fresh medium.

The cells at 3 days from the beginning of a subculture were suspended in an enzyme solution containing 1.0% Cellulase Onozuka (Yakult Honsha, Japan), 1.0% Macerozyme (Yakult Honsha, Japan), 0.1% Pectoriaze Y-23 (Seishin Seiyaku, Japan), 0.5% Dricellase (Kyowa Hakko, Japan) and 0.4 M mannitol, and the suspension was left to stand at 30° C. in the dark for 3 hours. The cell suspension was then filtered through 20 μm Nylon mesh and the obtained filtrate was centrifuged at 50×g for 5 minutes. The obtained precipitate of protoplasts was suspended in 0.4M mannitol and the protoplasts were washed twice with this solution.

The obtained protoplasts were suspended in EPAA buffer (Tada Y, Sakamoto M, Fujimura T: Efficient gene introduction into rice by electroporation and analysis of transgenic plants: use of electroporation buffer lacking chloride ions. Theor.Appl.Genet. 80:475–180 (1990)) and the suspension was left to stand in ice for 5 minutes. To the protoplast suspension, 10 μg of pGL2 plasmid and 30 μg of pPCK plasmid were added and electric pulse of 250 μF, 600 V/cm was applied to the suspension using an electroporation apparatus (Bio-Rad, USA). The pulse-treated protoplasts were left to stand in ice for 15 minutes and then at room temperature for 30 minutes.

Protoplasts were collected by centrifugation and suspended in R2-1 medium containing 1.25%. Seeplaque (trademark) agarose (FMC, USA) to a cell population of $3\times10^5$ cells/ml. The suspension was then solidified on 9 cm petri dish in the form of small droplets. To this, R2-1 medium and rice Oc cells (Baba A, Hasezawa S, Shono K: Cultivation of rice protoplasts and their transformation mediated by Agrobacterium spheroplast. Plant Cell Physiol. 27:463–471(1986)) were added and the resultant was cultured at 25° C. in the dark.

Two weeks after, the liquid medium and Oc cells were removed and R2-t medium was added, followed by culture at 25° C. under continuous illumination. One week after, the medium was replaced with R2-t medium containing 40 mg/l hygromycin and culture was continued. One week after, the agarose droplets containing calli with diameters of about 0.2–0.5 mm were disrupted together with small amount of sterilized water and the resultant was placed on N6-12 medium, followed by culturing the resultant at 25° C. under continuous illumination. When the calli grew to have a diameter of not less than 2 mm, the calli were transplanted to N6S3 medium containing 40 mg/l of hygromycin, and culture was further continued. Differentiated plants which grew to a height of not less than about 10 cm were transplanted to pots and cultivated in a green house.

Compositions of Media

2N6 Medium (pH 5.8)
N6 Basal Medium (Chu 1978)
Casamino Acid 1000 mg/ml
2,4-D 2.0 mg/ml
Sucrose 20000 mg/ml
Gelrite 2000 mg/ml N6 Liquid Medium (pH 5.8)
N6 Basal Medium
Casamino Acid 300 mg/ml
2,4-D 1.0 mg/ml
Sucrose 30000 mg/ml R2-1 Medium (pH 5.8)
R2 medium inorganic salts (Ohira et al.1973)
MS medium vitamins (Murashige and Skoog 1962)
Casamino Acid 1000 mg/ml
2,4-D 1.0 mg/ml
n-propyl gallate 0.05 mg/ml
Sucrose 68500 mg/ml
Glucose 36000 mg/ml R2-t medium (pH 5.8)
R2 medium inorganic salts
MS medium organic components
Casamino Acid 1000 mg/ml
2,4-D 1.0 mg/ml
Sucrose 20000 mg/ml
Glucose 10000 mg/ml N6-12 Medium (pH 5.8)
N6 basal medium
Casamino Acid 2000 mg/ml
2,4-D 0.2 mg/ml
6-BA. 0.5 mg/ml
ABA 5.0 mg/ml
Sucrose 20000 mg/ml
D-sorbitol 30000 mg/ml
Gelrite 2000 mg/ml N6S3 Medium
half concentrations of N6 medium major salts
N6 medium minor salts N6 medium vitamins AA medium amino acids (Toriyama and Hinata 1985)

Casamino Acid 1000 mg/ml

NAA 0.2 mg/ml

Kinetin 1.0 mg/ml

Sucrose 20000 mg/ml

Gelrite 3000 mg/ml

References

Chu,C.-C.(1978)The N6 medium and its application to anther culture of cereal crops. In Proc. Symp. Plant Tissue Culture. Peking: Science Press, pp.43–50; Murashige, T. and Skoog, F. (1962) A revised medium for rapid growth and bio assay with tobacco tissue culture. Physiol.Plant. 15:473–497;

Ohira, K., Ojima, K. and Fujiwara, A. (1973) Studies on the nutrition of rice cell culture I. A simple, defined medium for rapid growth in suspension culture. Plant Cell Physiol. 14:1113–1121;

Toriyama, K., Hinata, K. and Sasaki, T. (1986) Haploid and diploid plant regeneration from protoplasts of anther callus in rice. Theor.Appl. Genet. 73:16–19.

3. Localization of PCK Protein in Transformed Rice Plant

Materials and Methods

Main veins were removed from green leaves (5–10 g) of a transformed rice plant grown in an artificial weather chamber (28° C. day/22° C. night, long day regimen 16 hours) and the leaves were cut into pieces having 0.5–1 mm width. The obtained leaf pieces were digested in an enzyme solution containing 0.8% Cellulase Onozuka RS, 0.8% Fancellase (Yakult Honsha, Japan), 0.25% Pectriaze Y-23, 150 mM sodium phosphate buffer (pH 5.6), 0.3% bovine serum albumin and 0.4 M mannitol at 30° C. for 1 hour. The treated tissue was washed with a buffer (50 mM Hepes-KOH pH 7.0, 0.33 M sorbitol, 2 mM EDTA, 1 mM $MgCl_2$, 1 mM $MnCl_2$, 0.1% bovine serum albumin) and suspended in about 10 times volume of iced buffer containing 1 mg/ml sodium isoascorbate, followed by homogenization of the tissue with Polytron homogenizer (trademark, Kinematica, Switzerland). The homogenization with Polytron homogenizer was conducted twice at the highest power for 3 seconds. The obtained homogenate was filtered through 4-ply Miracloth (trademark, Calbiochem, USA) and the filtrate was quickly centrifuged (revolution was decreased when it reached 6000×g). The obtained precipitate was suspended in a buffer and the resultant was used as a chloroplast sample. To this sample, trypsin was added to a concentration of 50 $\mu$g/ml and the mixture was left to stand in ice for 30 minutes. After this trypsin treatment, chloroplasts were collected by centrifugation at 10,000×g for 3 minutes and suspended in 50 mM Hepes-KOH buffer (pH 8.0). The suspension was frozen at −80° C. and then thawed at room temperature to disrupt the chloroplasts. The disrupted chloroplasts were centrifuged at 10,000×g for 5 minutes and the obtained supernatant (soluble fraction of chloroplasts) was subjected to SDS-PAGE. After the electrophoresis, proteins in the gel were electrophoretically transferred to a nitrocellulose membrane and the PCK protein was detected by using anti-*U. panicoides* PCK protein rabbit antiserum, peroxidase-labeled anti-rabbit IgG goat antibody (MBL) and HRP coloring kit (trademark, Bio-Rad, USA).

Results

In the soluble fraction of the isolated chloroplasts, a PCK protein having a size corresponding to the size of processed transit peptide was detected. Since PCK protein was not decomposed by the trypsin treatment of the isolated chloroplasts, it is thought that PCK protein had been transported into the chloroplasts (stroma fraction).

4. Measurement of PCK Activity of Transformed Rice

Materials and Methods

All of the following operations were carried out at 4° C. About 0.2 g each of green leaves of rice transformants (PKS12 and PKS18) was pulverized with pestle and mortar together with 1 ml of an extraction buffer (50 mM HEPES-KOH pH 7.0, 2 mM $MnCl_2$, 2 MM $MgCl_2$, 1 mM EDTA, 0.1% (v/v) 2-mercaptoethanol, 1 mM PMSF, 1 MM benzamidine, 1 mM 6-amino-n-caproic acid, 10% (w/v) glycerol, 0.2% (w/v) sodium isoascorbate, 2% (w/v) Polycral AT). The obtained pulverized solution was centrifuged at 15,000×g for 20 minutes and the obtained supernatant was applied to NAP5 (trademark) column (Pharmacia, Sweden) preliminarily equilibrated with a column buffer (25 mM HEPES-KOH pH 7.0, 2 mM $MnCl_2$, 2 mM $MgCl_2$, 0.1% (v/v) 2-mercaptoethanol, 10% (w/v) glycerol) to carry out desalination, thereby obtaining a crude extract. Quantitation of chlorophyll in the pulverized solution was carried out in accordance with the method of Wintermans and deMots (Wintermans JFGM, De Mots A: Spectrophotometric characteristics of chlorophylls a and b and their pheophytins in ethanol. Biochem.Biophys. Acta 109:448–453(1965)). Quantitation of proteins in the crude extract was carried out by using Protein Assay kit (trademark, Bio-Rad, USA) according to Bradford's method (Bradford MM: A rapid and sensitive method for quantitation of microgram quantities of protein utilizing the principle of protein-dye binding. Anal. Biochem. 72:248–254(1976)). Measurement of phosphoenolpyruvate carboxykinase was carried out by measuring the rate of decrease in absorption of oxaloacetic acid at 280 nm of 1 ml of the reaction mixture containing 25 mM HEPES-KOH pH 7.5, 4 mM DTT, 0.2 mM oxaloacetic acid, 1 unit of pyruvate kinase, 0.2 mM ATP and 50 $\mu$l of the crude extract.

Results

PCK activity was detected in the crude extract of green leaves of transformed rice and non-transformed rice. However, in the non-transformed rice, substantially no PCK activity was detected.

TABLE 2

Phosphoenolpyruvate Carboxykinase Activity of Transformed Rice

| Transformant | Enzyme Activity (units/mg/chlorophyll) |
| --- | --- |
| PKS12 | 1.61 |
| PKS18 | 2.99 |
| Control 1 | 0.00 |
| Control 2 | 0.00 |

These results show that active PCK protein is localized in chloroplasts of transformed rice plants to which a chimeric gene prepared by adding a sequence encoding the transit peptide of rice Rubisco small subunit to the cDNA encoding the PCK protein isolated from *U. panicoides* was introduced.

What is claimed is:

1. A cloned DNA which encodes the amino acid sequence shown in SEQ ID NO: 2.

2. A cloned DNA which encodes the amino acid sequence from 57th amino acid serine to the C-terminal of the amino acid sequence shown in SEQ ID NO: 2.

3. A cloned DNA which encodes the amino acid sequence from 61st amino acid glutamic acid to the C-terminal of the amino acid sequence shown in SEQ ID NO: 2.

4. A cloned which encodes the amino acid sequence from 66th amino acid leucine to the C-terminal of the amino acid sequence shown in SEQ ID NO: 2.

5. A cloned DNA which encodes the amino acid sequence from 69th amino acid glycine to the C-terminal of the amino acid sequence shown in SEQ ID NO: 2.

6. A cloned DNA which encodes the amino acid sequence from 75th amino acid glycine to the C-terminal of the amino acid sequence shown in SEQ ID NO: 2.

7. A cloned DNA which encodes the amino acid sequence shown in SEQ ID NO: 4.

8. A cloned DNA which encodes the amino acid sequence from 57th amino acid serine to the C-terminal of the amino acid sequence shown in SEQ ID NO: 4.

9. A cloned DNA which encodes the amino acid sequence shown in SEQ ID NO: 6.

10. A cloned DNA which encodes the amino acid sequence from 52nd amino acid serine to the C-terminal of the amino acid sequence shown in SEQ ID NO: 6.

11. A recombinant vector comprising said DNA according to any one of claims 1, 2, 3, 4, 5, 6, 7, 8, 9 and 10, wherein said recombinant vector can express said DNA in a host cell.

12. A plant transformed with said recombinant vector according to claim 11, which produces phosphoenolpyruvate carboxykinase.

13. The plant according to claim 12, which is rice.

* * * * *